(12) United States Patent
Kwon et al.

(10) Patent No.: US 10,473,093 B2
(45) Date of Patent: Nov. 12, 2019

(54) SOFT ACTUATOR USING THERMOELECTRIC EFFECT

(71) Applicant: Daegu Gyeongbuk Institute of Science and Technology, Daegu (KR)

(72) Inventors: Oh-Seok Kwon, Busan (KR); Sung Mok Ha, Gyeongsangnam-do (KR); Youn Ho Choi, Daegu (KR); Dong Ha Lee, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 82 days.

(21) Appl. No.: 15/659,784

(22) Filed: Jul. 26, 2017

(65) Prior Publication Data

US 2018/0058429 A1 Mar. 1, 2018

(30) Foreign Application Priority Data

Aug. 26, 2016 (KR) .................. 10-2016-0109447
Sep. 23, 2016 (KR) .................. 10-2016-0122107
(Continued)

(51) Int. Cl.
*F03G 7/06* (2006.01)
*H01L 35/32* (2006.01)
(Continued)

(52) U.S. Cl.
CPC .............. *F03G 7/06* (2013.01); *A61B 34/30* (2016.02); *A61F 2/68* (2013.01); *H01L 35/325* (2013.01);
(Continued)

(58) Field of Classification Search
CPC .... F03G 7/06; F03G 7/065; A61F 2/08; A61F 2002/0894; A61F 2002/5066;
(Continued)

(56) References Cited

U.S. PATENT DOCUMENTS

| 7,188,473 B1* | 3/2007 | Asada ..................... F03G 7/065 |
| | | 310/306 |
| 2015/0240793 A1* | 8/2015 | Safai ..................... F03G 7/065 |
| | | 60/527 |

(Continued)

FOREIGN PATENT DOCUMENTS

| JP | 6101625 A | 4/1994 |
| JP | 1193827 A | 4/1999 |

(Continued)

OTHER PUBLICATIONS

Haines, C.S. et al., "Artificial Muscles from Fishing Line and Sewing Thread," Science, vol. 343, No. 6173, (Feb. 21, 2014), pp. 868-872.

(Continued)

*Primary Examiner* — Mark A Laurenzi
*Assistant Examiner* — Xiaoting Hu
(74) *Attorney, Agent, or Firm* — Fredrikson & Byron, P.A.

(57) ABSTRACT

The present invention relates to a soft actuator moving linearly against external stimuli whose expansion and contraction can be actively controlled, suggesting that the actuator of the invention overcomes the problems of the conventional soft actuators, The soft actuator of the present invention can be repetitively driven quickly and accurately by controlling heating and cooling by using thermoelectric effect and, the soft actuator of the present invention can realize bending, tensioning, compression, and rotational driving of a tubular device containing a driver.

2 Claims, 24 Drawing Sheets

(30) Foreign Application Priority Data

| | | |
|---|---|---|
| Sep. 23, 2016 | (KR) | 10-2016-0122112 |
| Sep. 23, 2016 | (KR) | 10-2016-0122116 |
| Dec. 8, 2016 | (KR) | 10-2016-0166575 |
| Dec. 8, 2016 | (KR) | 10-2016-0166587 |

(51) Int. Cl.

| | |
|---|---|
| *A61B 34/30* | (2016.01) |
| *A61F 2/68* | (2006.01) |
| *A61H 1/02* | (2006.01) |
| *A61F 2/08* | (2006.01) |
| *A61F 2/48* | (2006.01) |
| *A61F 2/50* | (2006.01) |

(52) U.S. Cl.

CPC .......... *A61B 2034/301* (2016.02); *A61F 2/08* (2013.01); *A61F 2002/0894* (2013.01); *A61F 2002/482* (2013.01); *A61F 2002/5066* (2013.01); *A61H 1/024* (2013.01); *A61H 1/0277* (2013.01); *A61H 2201/1207* (2013.01); *A61H 2201/1481* (2013.01); *A61H 2201/1664* (2013.01)

(58) Field of Classification Search

CPC ............... A61F 2002/482; A61B 34/30; A61B 2034/301; A61H 1/024; A61H 1/0277; A61H 2201/1207; H01L 35/325

See application file for complete search history.

(56) References Cited

U.S. PATENT DOCUMENTS

| | | | | |
|---|---|---|---|---|
| 2015/0280099 | A1* | 10/2015 | Boukai | H01L 35/32 |
| | | | | 136/203 |
| 2017/0035550 | A1* | 2/2017 | Hiraoka | A61F 2/08 |

FOREIGN PATENT DOCUMENTS

| | | |
|---|---|---|
| JP | 2000135288 A | 5/2000 |
| JP | 200586981 A | 3/2005 |
| KR | 1020070116405 A | 12/2007 |
| KR | 1020150038475 A | 8/2013 |
| KR | 1020160039170 A | 4/2016 |
| KR | 1020160091656 A | 8/2016 |

OTHER PUBLICATIONS

Ha, SM et al., "fiber-based soft actuator design," DGIST, (Nov. 2016), pp. 637-639, with English Abstract.
Haines, C.S. et at, "Artificial Muscles from Fishing Line and Sewing Thread," Science, vol. 343, No. 6173, pp. 868-872.
Abstract for Korean Publication No. 10-2015-0038475 A, published Apr. 8, 2015, 2 pgs.
Abstract for Korean Publication No. 10-2016-0091656 A, published Aug. 3, 2016, 1 pg.
Abstract for Korean Publication No. 10-2007-0116405 A, published Dec. 10, 2007, 1 pg.
Abstract for Japanese Publication No. 06-101625 A, published Apr. 12, 1994, 1 pg.
Abstract for Korean Publication No. 10-2016-0039170 A, published Apr. 8, 2016, 1 pg.
Hanes, C. et al., "Artificial Muscles from Fishing Line and Sewing Thread," Science, vol. 343, (Feb. 21, 2014) pp. 868-872.
English Abstract and Machine Translation for Korean Publication No. 10-2016-0091656 A, published Aug. 3, 2016, 37 pgs.

* cited by examiner

【Figure 1】
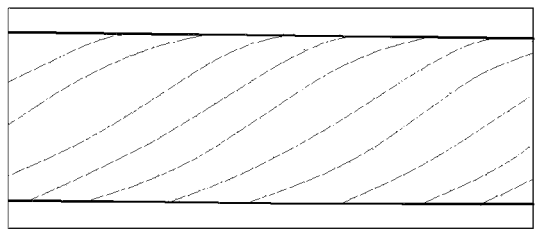
【Figure 2】
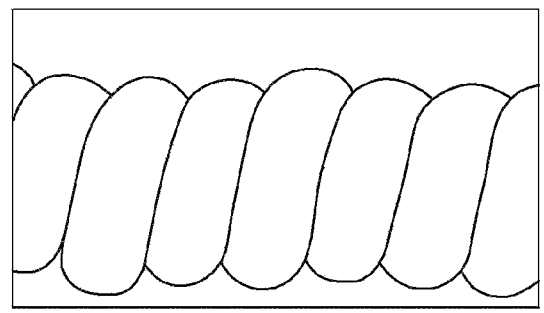

【Figure 3】
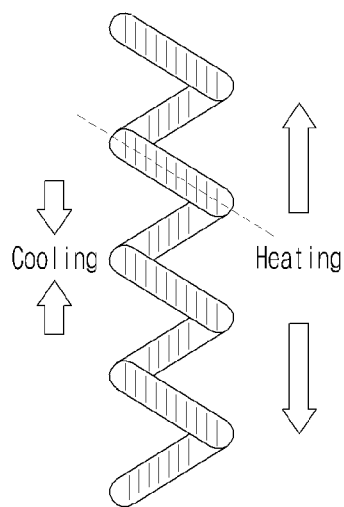

【Figure 4】
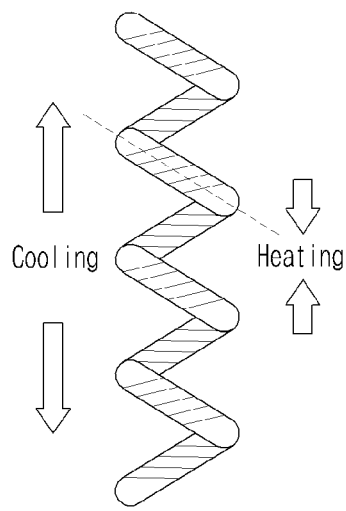
【Figure 5】
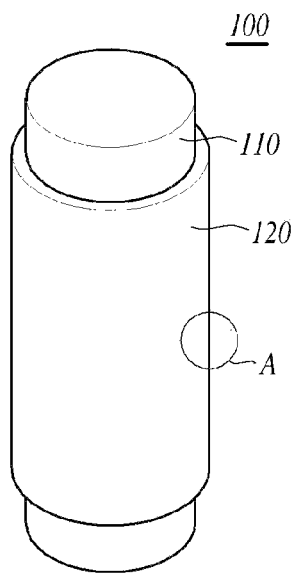

【Figure 6】
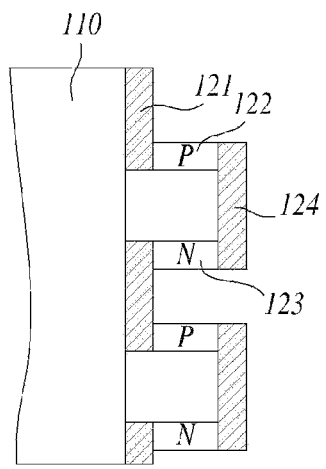
【Figure 7】
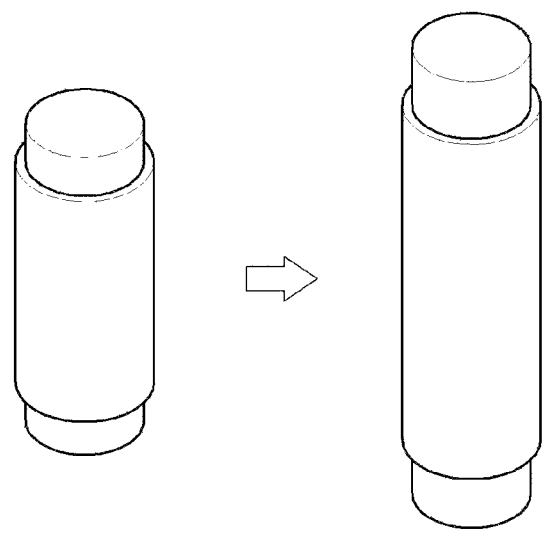

【Figure 8】
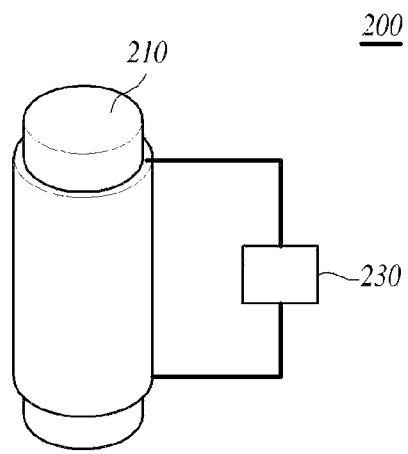
【Figure 9】
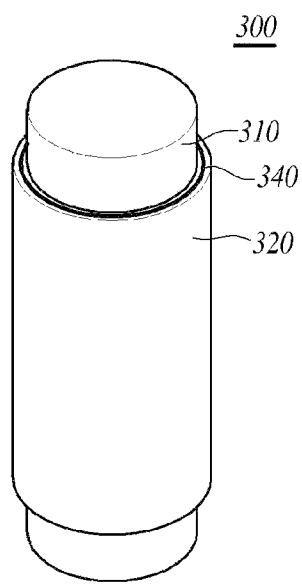

【Figure 10】
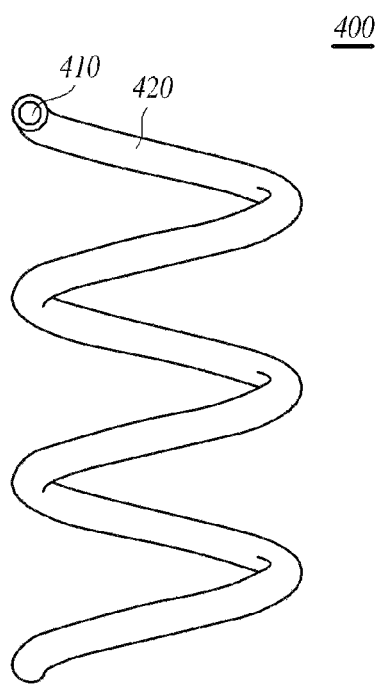

【Figure 11】
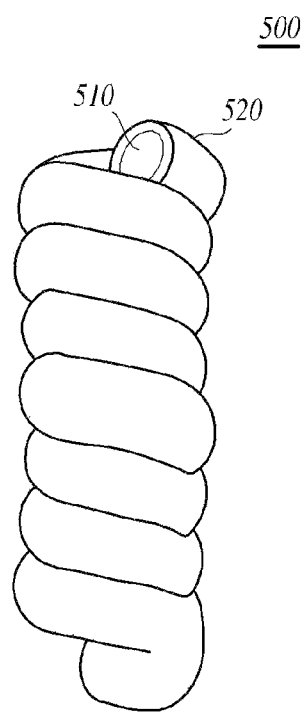

【Figure 12】
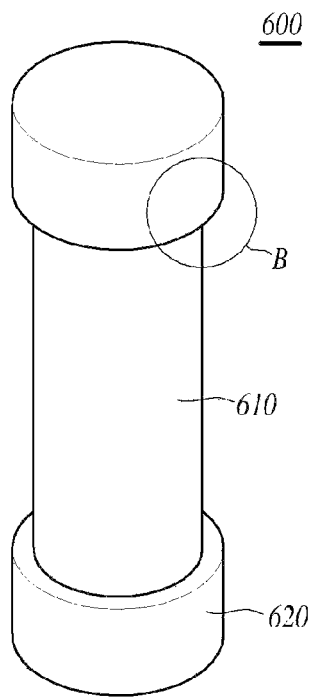
【Figure 13】
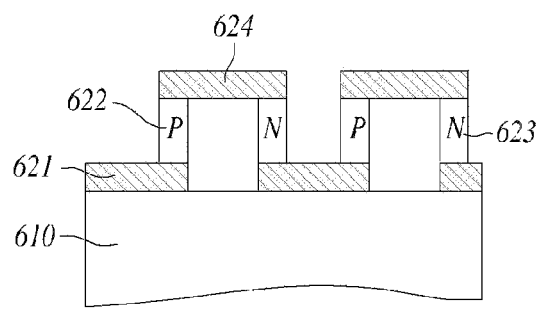

【Figure 14】
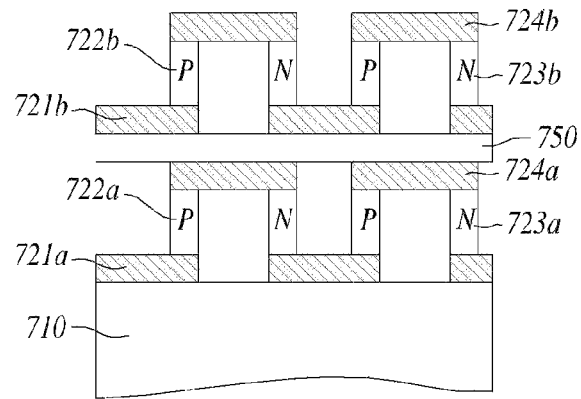
【Figure 15】
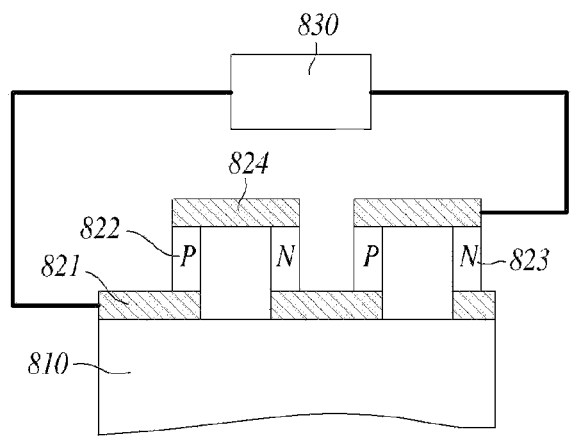
【Figure 16】
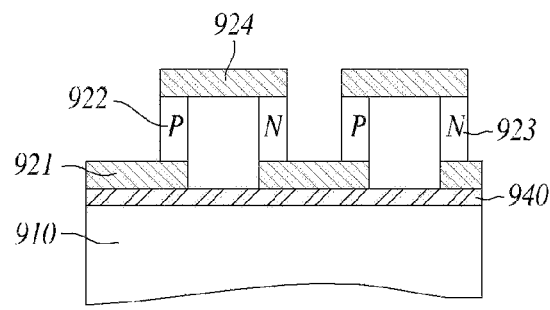

【Figure 17】
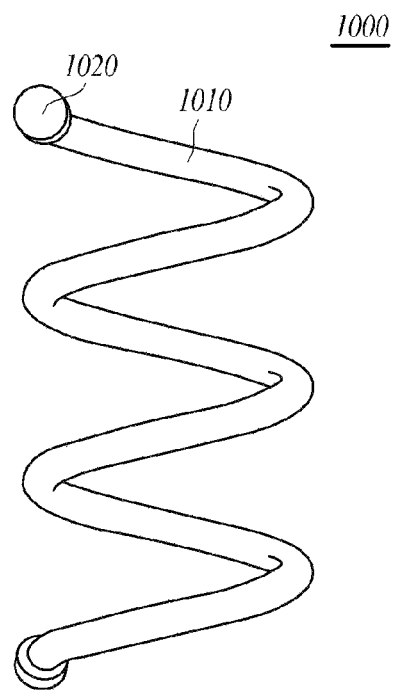

【Figure 18】
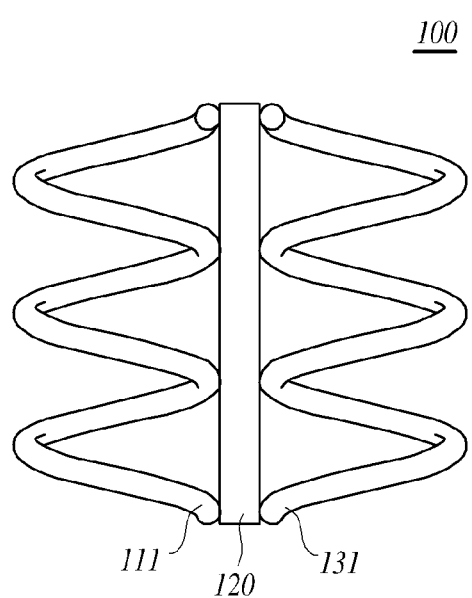

【Figure 19】
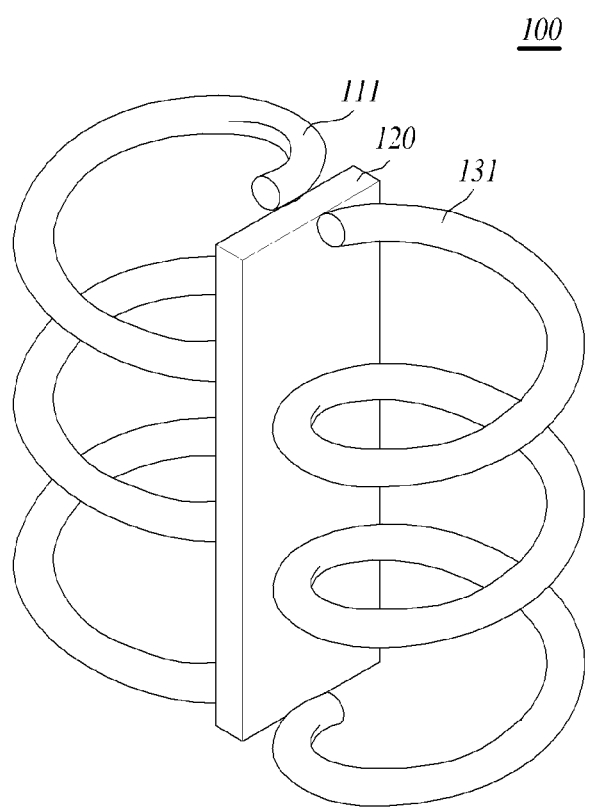

【Figure 20】
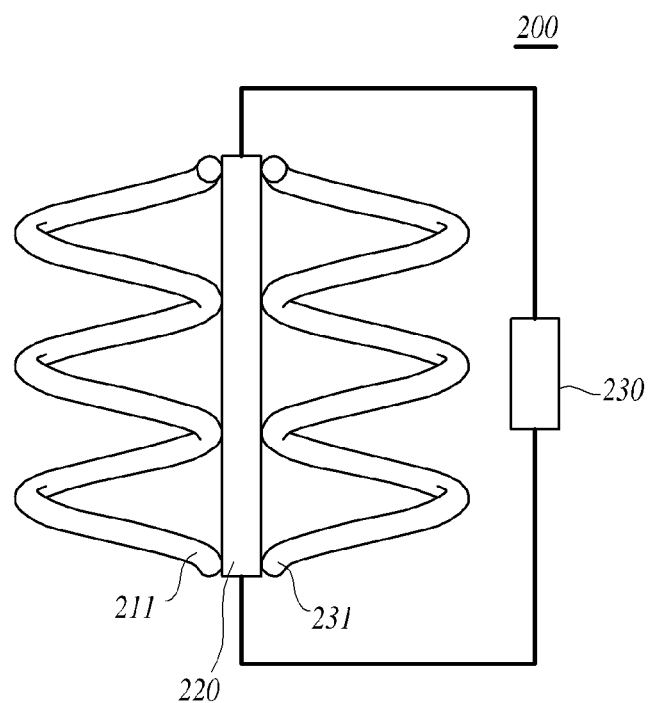

【Figure 21】
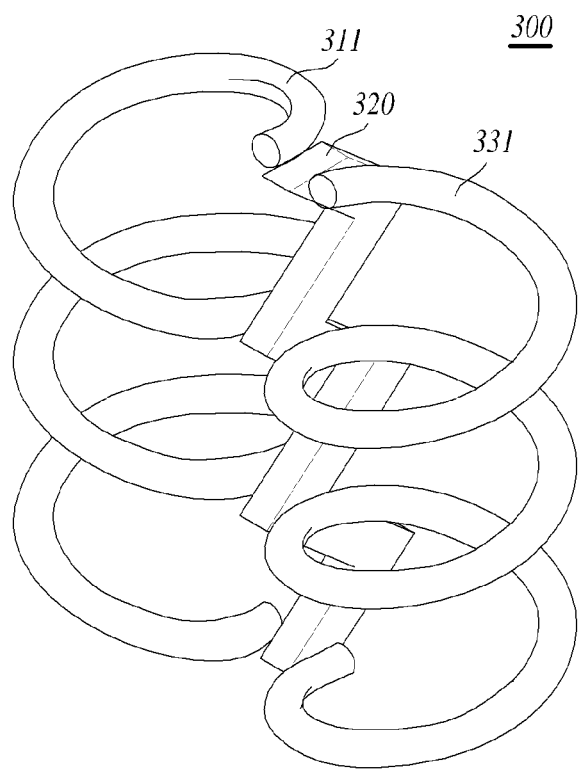

[Figure 22]
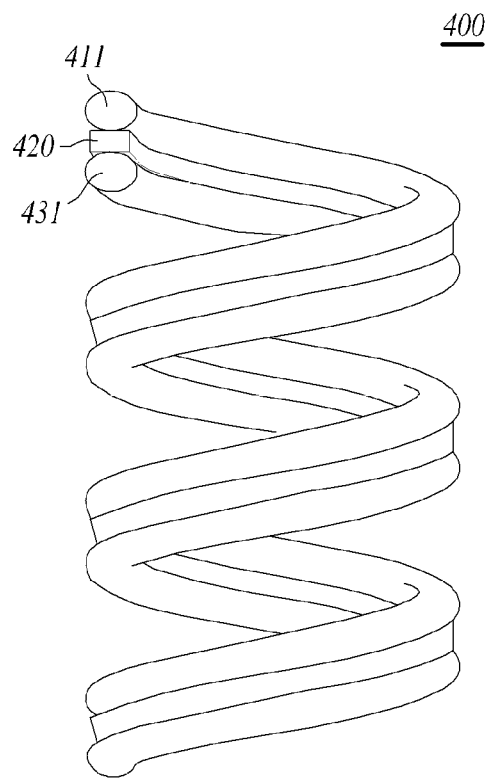

【Figure 23】
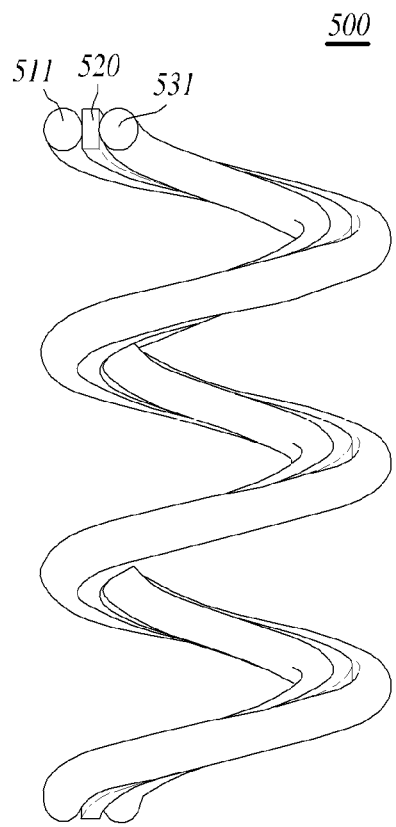

【Figure 24】
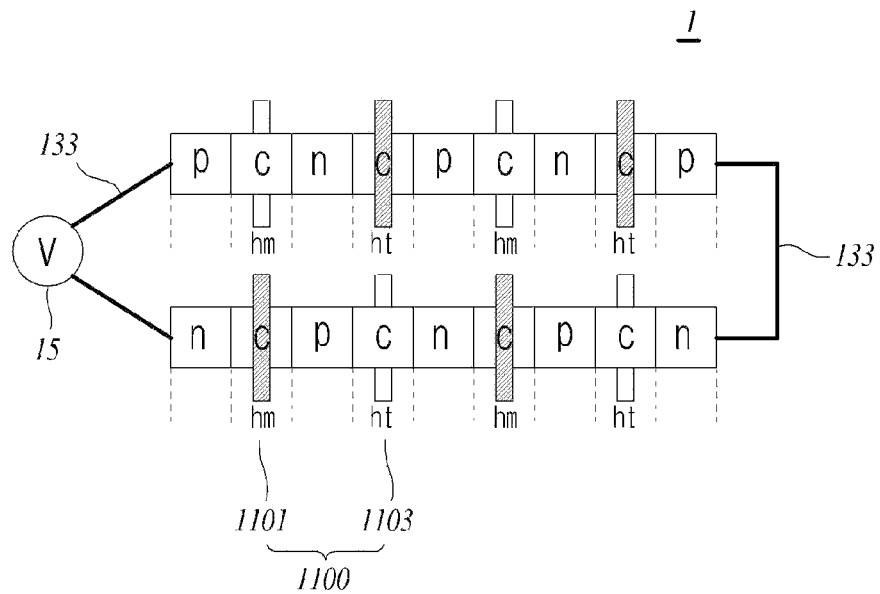
【Figure 25】
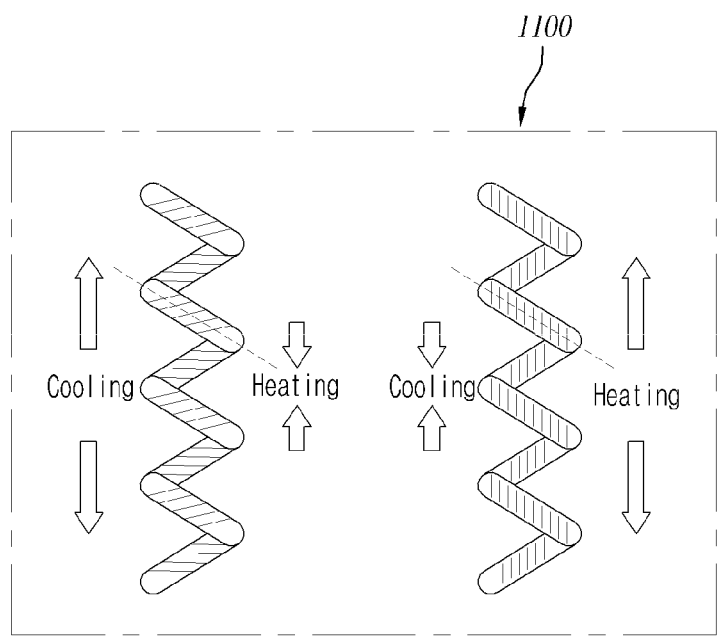

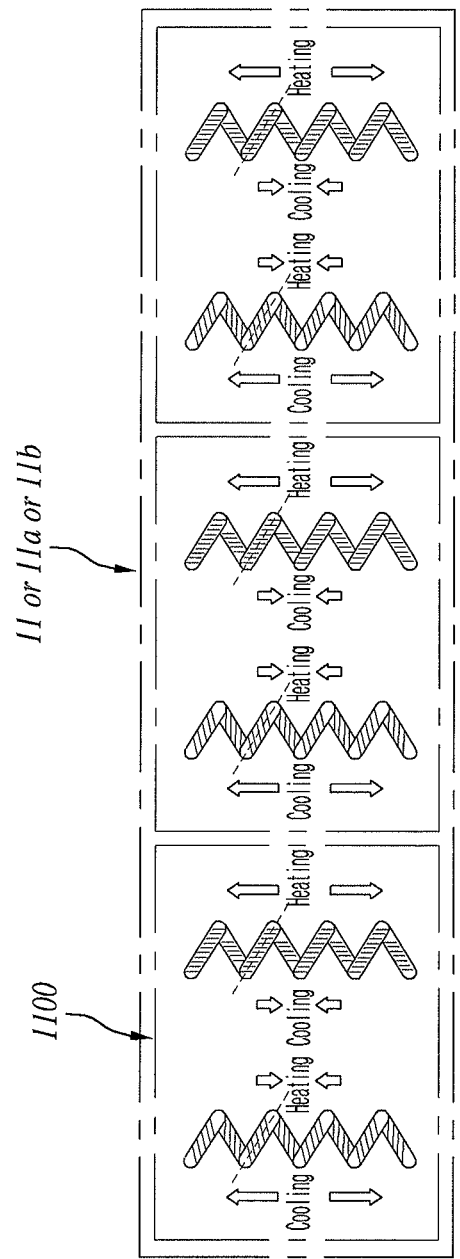
[Figure 26]

【Figure 27】
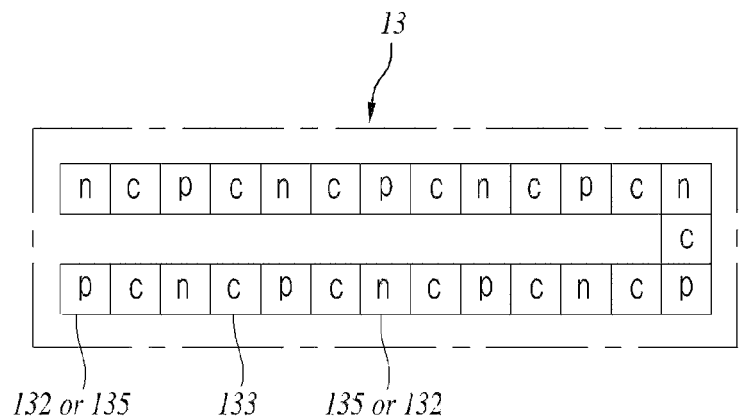
132 or 135    133    135 or 132
【Figure 28】
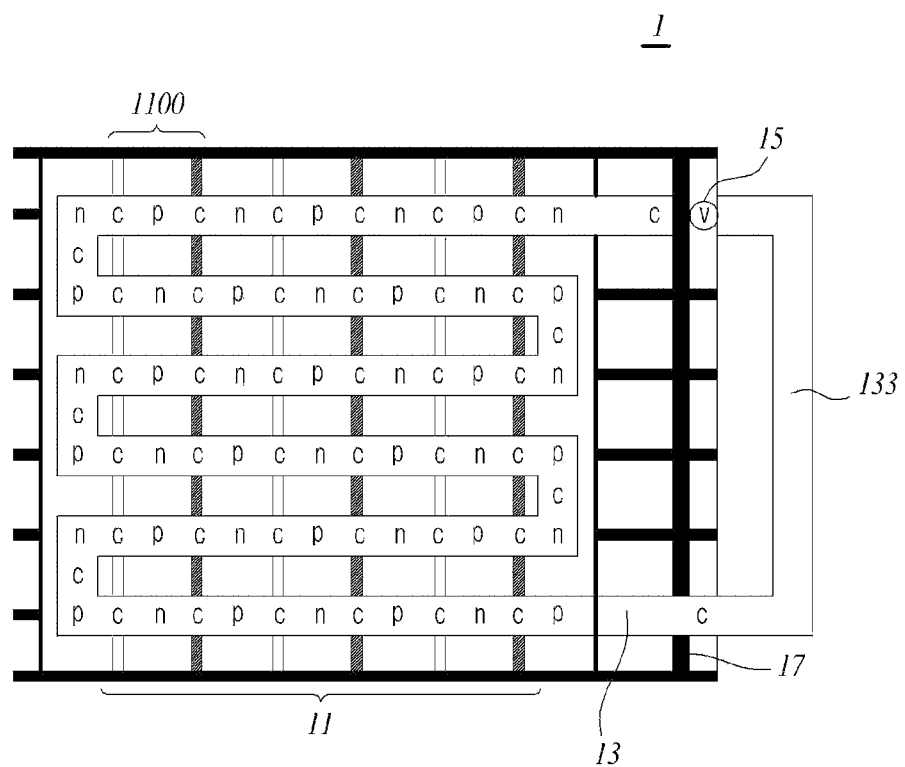

【Figure 29】
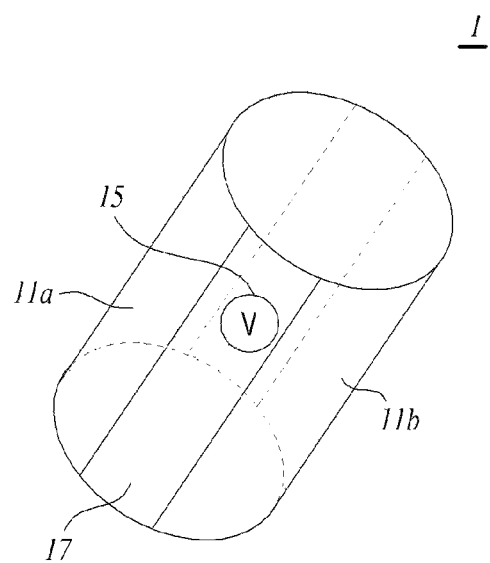

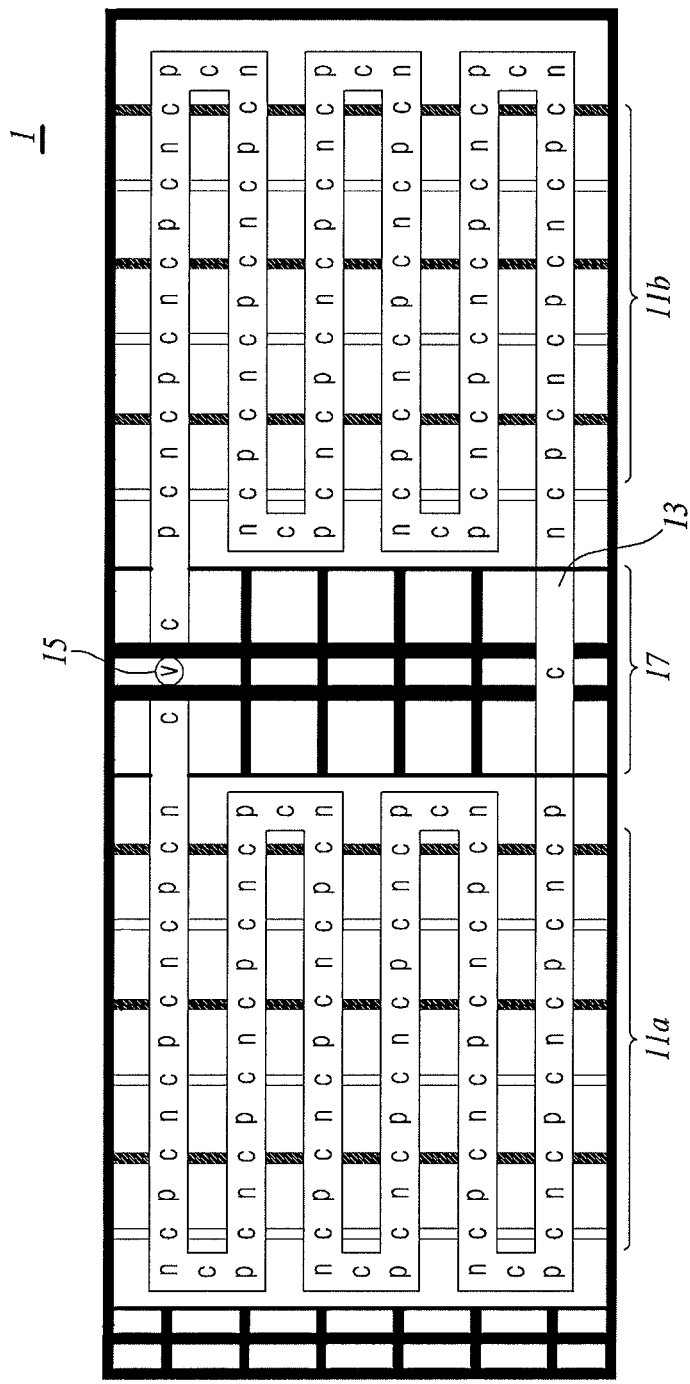
[Figure 30]

【Figure 31】
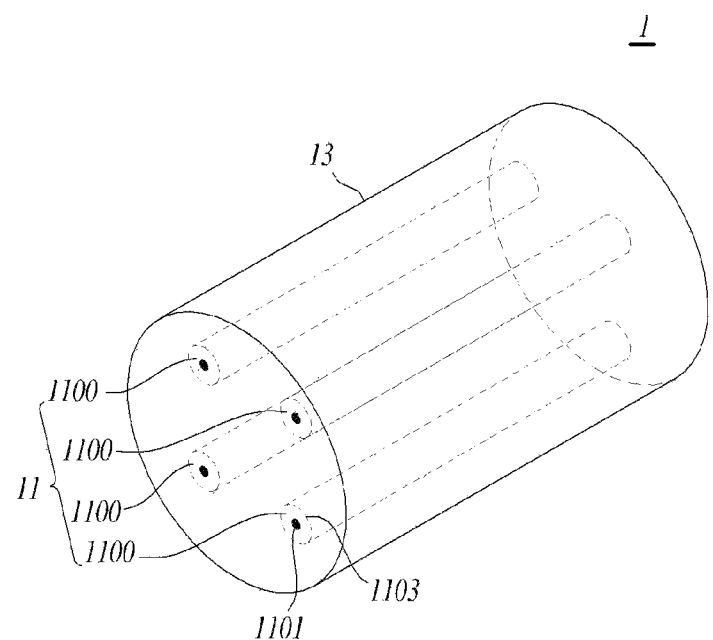
【Figure 32】
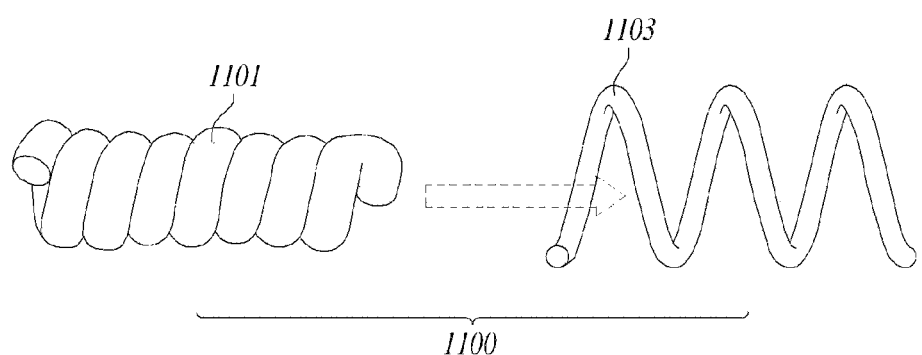

【Figure 33】
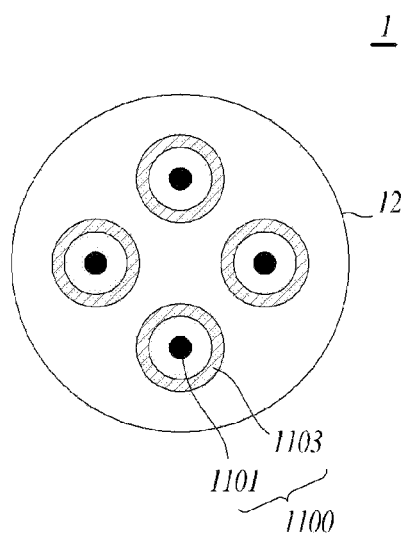
【Figure 34】
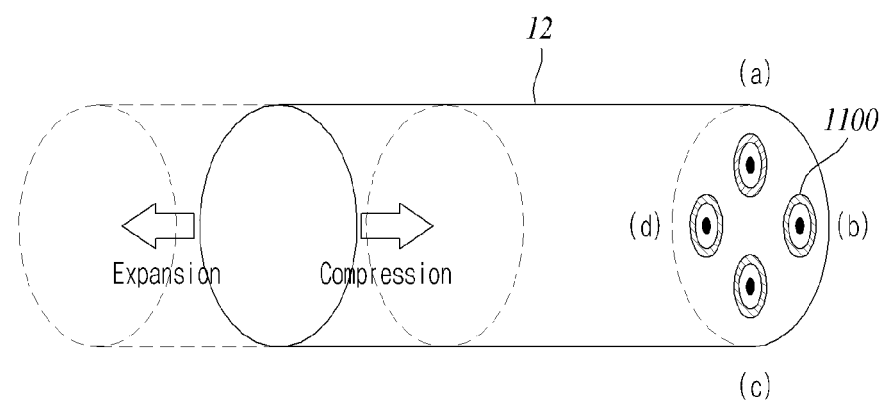

【Figure 35】
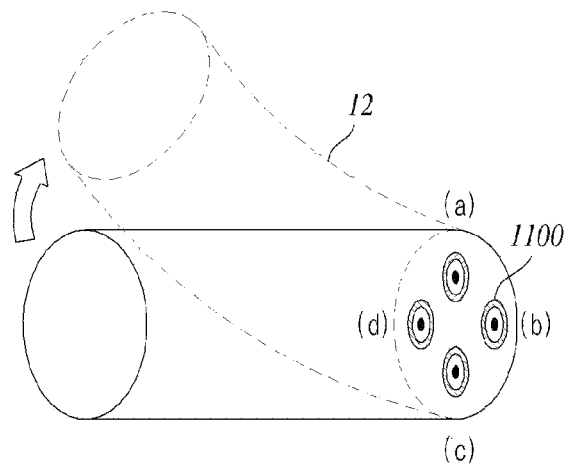
【Figure 36】
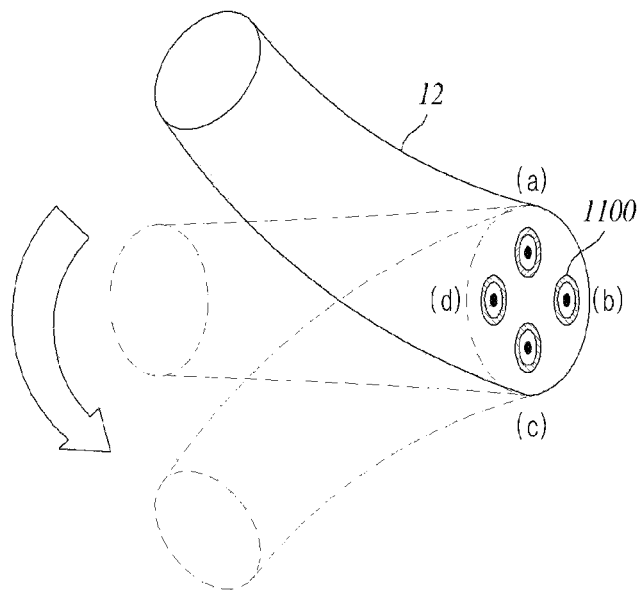

SOFT ACTUATOR USING THERMOELECTRIC EFFECT

BACKGROUND OF THE INVENTION

1. Field of the Invention

The present invention relates to a soft actuator.

2. Description of the Related Art

An actuator indicates a driving device that drives a machine using power. The actuator may refer to an electric motor or any hydraulic or pneumatically actuated piston or cylinder device having any type of control mechanism in the mechatronics field. In recent years, a soft actuator or a micro actuator, which can be applied to artificial muscles, has been recently developed using a new material.

A soft actuator is a flexible apparatus that can deliver the entered power or displacement through a flexible body, unlike the conventional mechanism that delivers the entered power or displacement through the conventional rigid body.

The soft actuator is largely divided as follows: a bistable actuator using a jump phenomenon to move from an unstable point to a stable point by arranging the potential wells at two locations; a conductive polymer actuator using an electroactive polymer; and a string reinforced actuator using a string twist like the target technology.

The string reinforced actuator is classified according to the direction of string movement.

In general, a soft actuator that is driven by an external stimulus including a string reinforced actuator uses electricity, temperature, and light applied at one end as an external stimulus source.

In particular, there is a method to give a temperature stimulus to a soft actuator by using Joule heat. Joule heat can be explained as a phenomenon in which heat is generated when current flows through a highly resistant wire. The reason why Joule heat is generated is that free electrons in the wire actively move and cause many collisions with atoms, and the kinetic energy of the atoms is converted into heat energy due to the collision. At this time the heat generated by the resistance is called Joule heat. In other words, Joule heat is the heat converted from electric energy. In electrical wiring or transmission lines in the general machinery, Joule heat causes a huge energy loss therein. So, it is important to draw a plan that can minimize the generation of Joule heat. Also, Joule's law is established with regard to the consumption of electric energy that can produce Joule heat.

When a soft actuator is driven by using Joule heat, fast temperature change can be induced during the actuator is heated by the generation of Joule heat, but the temperature change is going to be very slow during the cooling, which draws a limitation in the driving of the actuator.

In relation to the prior arts involved in a soft actuator, Korean Patent Publication No 10-2016-0091656 (referred 'prior art' hereinafter) describes 'Torsional actuators by temperature gradient and energy harvesting device using the same'. The prior art takes the heat energy possibly with temperature gradient that can be obtained from an outer environment as a power source to operate the soft actuator. That is, there is a difficulty in inducing the operation of the additional configuration due to the driver because it does not adopt an additional configuration for driving the driver.

Therefore, the present inventors developed a soft actuator that contains an additional configuration to supply energy in order to control the actuator and can overcome the disadvantages of the conventional actuator using Joule heat by using thermoelectric heat instead.

In the meantime, an actuator can be used to drive a catheter. The catheter is one of the common names of tubular instruments, and can be made of different materials in different sizes and shapes according to the purpose of use. The use of the catheter is to discharge the fluid in the body cavity or various organs, aspirate the perfusion fluid for cleaning, measure the cardiovascular behavior or central venous pressure, and inject the drug or contrast agent into the body An actuator can also be used to drive an endoscope. The endoscopy is a device designed to observe such an organ that is hard to observe its lesions without surgery or autopsy by inserting a machine therein. Commonly used endoscope types include bronchoscope, esophagoscope, gastroscope, duodenoscope, rectoscope, cystoscopy, and laparoscope. Other special cases include thoracoscopy, mediastinoscope, and cardioscope. The endoscope can be in the form of a direct scope that is the shape of one tube through which an organ can be observed with the naked eye, or uses a lens system, or is equipped with a camera, or can be in the form of a string scope using a glass string. A gastrocamera can be used to detect and diagnose fine stomach lesions by inserting a small camera in the stomach and directly photographing and recording the stomach mucosa. In the meantime, a gastrostringscope has an excellent resolving power and can be equipped with an apparatus capable of cutting the lesional tissue directly while observing for further examination.

The tube type actuator can be realized in various ways. A bimetal method is the most representative example. The bimetal method is a method using a metal with two kinds of thin metal plates which are different in degree of expansion by heat. The metal is mainly formed by depositing a metal layer on a $SiO_2$ layer (insulating layer) on which a current path made of polysilicon is buried. Since the thermal expansion coefficient of the $SiO_2$ layer (insulating layer) is different from that of the metal layer, when voltage is applied to the thermal micro-actuator, a displacement is generated in the side having a small coefficient of thermal expansion and is driven in such a manner as to bend.

Another type of the actuator is the differential resistance type. The differential resistance type actuator is made of polysilicon, the single material. The differential resistance type actuator is composed of a high temperature part and a low temperature part having electrodes to which voltage is applied. The high temperature part has a small cross-sectional area, the low temperature part has a large cross-sectional area, and is configured so that the opposite ends of the side having the electrode are connected to each other. When voltage is given to the electrode of the low temperature part and the high temperature part not connected to the differential resistance type actuator, current flows through the pathway comprising the high temperature part and the low temperature part. By the difference of the area between the high temperature part and the low temperature part, the difference in resistance is caused and accordingly the different level of Joule heat is generated. As a result, the temperature becomes different between the high temperature part and the low temperature part. In the differential resistance type actuator, the difference in thermal expansion is caused by the difference of the temperature and as a result, displacement moves to cause bending from the high temperature part to the low temperature part.

In relation to the prior arts involved in the actuator, Korean Patent No 10-0789268 (referred 'prior art' hereinafter) describes "Thermal expansion micro actuator, micro mirror formed directly on the same, micro mirror actuating apparatus using thermal expansion micro actuator, and light-switch using the same". However, this prior art has a problem that the driving direction is limited to the driving in which the driving direction is biased in both directions with respect to the single axis as the driving device that is driven in accordance with the expansion ratio of the high temperature part and the low temperature part.

PRIOR ART REFERENCE

Patent Reference

Korean Patent Publication of unexamined applications No. 10-2015-0038475
Korean Patent Publication No. 10-2016-0091656
Korean Patent No. 10-0789268

SUMMARY OF THE INVENTION

It is an object of the present invention to provide a soft actuator that can reduce the operation response time of the soft actuator by converting the natural cooling dependent operation into the forced cooling dependent operation.

It is another object of the present invention to overcome the problems of the conventional soft actuator in order to provide a new actuator whose expansion and contraction can be actively controlled and movement is forced linearly according to external stimuli.

It is also an object of the present invention to provide a soft actuator that can drive repetitively, fast and accurately, by controlling heating and cooling using thermoelectric effect.

It is further an object of the present invention to provide a soft actuator for the realization of bending, tensioning, compression, and rotation of a tubular device including a driver.

The soft actuator according to an example of the present invention includes a string that is contracted or expanded by heating or cooling; and a thermoelectric element that can heat or cool the string as arranged at least one side of the string.

The string may further have twist or twist and coiling feature.

The thermoelectric element can be arranged at least on a portion of the surface of the string.

At this time, a control unit to control the direction of current flowing through the thermoelectric element can be additionally included.

Also, an adhesive layer connecting the surface of the string and the thermoelectric element can be additionally included.

The thermoelectric element can be expanded or contracted by the expansion and contraction of the string.

The method for preparing the soft actuator according to an example of the present invention comprises the steps of preparing a string that is twisted; and arranging a thermoelectric element at least on a portion of the surface of the string.

The method above can additionally include a step of coiling the string before the step of arranging the thermoelectric element at least on a portion of the surface of the string.

The method above can additionally include a step of coiling the string after the step of arranging the thermoelectric element at least on a portion of the surface of the string.

The soft actuator according to an example of the present invention includes the first string and the second string having twist; and the thermoelectric element arranged in between the first string and the second string.

The first string above is showing forward reaction by the thermoelectric element and the second string above is showing reverse reaction by the thermoelectric element.

The first and the second strings and the thermoelectric element above can be coiled.

The first and the second strings and the thermoelectric element above can be arranged horizontally.

The first and the second strings and the thermoelectric element above can be arranged vertically.

The thermoelectric element above can heat or cool down the side of the string.

The thermoelectric element can control the movement of the string by regulating the temperature of the string surface by heating or cooling.

The thermoelectric element above can also be flexible.

The soft actuator according to an example of the present invention contains the thermoelectric element arranged on one side of the string and can be expanded or contracted according to the change of the direction of current flowing through the thermoelectric element.

At this time, the thermoelectric element can be laminated in multiple layers.

Also, an adhesive layer connecting the surface of the string and the thermoelectric element can be additionally included.

A control unit can also be additionally included to connect the thermoelectric element to one side of the string.

The soft actuator according to an example of the present invention comprises a driving part composed of the first string that can be contracted or expanded by heating or cooling and the second string that moves against the first string by heating or cooling wherein the strings are arranged not to be contacted with each other while both making one unit; and a thermoelectric element part that heats or cools the driving part, in which a conductor region is arranged against the driving part in order to heat or cool the first string and the second string.

Preferably, the soft actuator can additionally include a power supply part that can form a closed circuit together with the thermoelectric element part and can supply current to the thermoelectric element part.

Preferably, the soft actuator of the invention can additionally include a string part composed of flexible strings that is arranged in parallel to the side of the unit above.

Preferably, the thermoelectric element part is crossed over the top side or the bottom side of the first string and the second string and the first string and the second string are arranged facing opposite each other from the thermoelectric element part as a center.

Preferably, the driving part may cool any one of the first string and the second string with the heat energy transferred from the thermoelectric element part and heat the other string so that the unit body can realize a single drive.

Preferably, the driving part has multiple units arranged in parallel.

Preferably, the thermoelectric element part comprises the first conductive body, the second conductive body that generates another heat flow to the different direction from the one induced by the first conductive body, and the conductor arranged in between the first conductive body and the second conductive body in parallel.

Preferably, the thermoelectric element part can heat or cool down the conductor since it has two separated conduction pathways through which current flows through the first conductive body, passes through the conductor and then arrives at the second conductive body; and current flows through the second conductive body, passes through the conductor and then arrives at the first conductive body.

Preferably, the driving part accomplishes a single drive since the first string and the second string is contracted or expanded by heating or cooling the conductor.

Preferably, in the driving part, a driving surface is formed by arranging a plurality of the unit bodies in parallel; and the driving surface forms a cylindrical side wall together with the string part composed of flexible strings that is connected to the side of the unit above in parallel, side by side. The thermoelectric element part has a conduction pathway on one side of the driving surface through which current flows through the first conductive body, passes through the conductor and arrives at the second conductive body; and the other conduction pathway on the other side of the driving surface through which current flows through the second conductive body, passes through the conductor and arrives at the first conductive body. This pair of the driving surface realizes different movements of contraction or expansion when current is provided from the thermoelectric element part, and as a result it can create bending moment.

The soft actuator according to an example of the present invention characteristically comprises a driving part composed of the first string having twist and coiling and can be contracted or expanded by heating or cooling and the second string having twist and coiling and can be contracted or expanded by heating or cooling and is arranged with maintaining distance from the first string; and a driving cable having a hollow in which the unit body is intruded.

Preferably, in the driving part, one of the strings, the first string and the second string, is the homochiral string wherein twist and coiling are made in the same direction and the other is the heterochiral string wherein twist and coiling are made in different direction.

Preferably, the driving part includes an electric heating body to generate heat by using the applied current and the electric heating body herein can deliver heat energy to the first string and the second string.

Preferably, in the driving part, the first string and the second string which forms the unit can be driven differently by contraction or expansion when they are heated or cooled down.

Preferably, the driving part may include a plurality of unit bodies, and the driving cable may include a plurality of hollows corresponding to the number of the unit bodies.

Preferably, in the driving part, the driving of the plurality of unit bodies is controlled independently to enable tension, compression, bending, and rotation of the driving cable.

Advantageous Effect

The soft actuator according to an example of the present invention and the method for preparing the same can reduce the operation response time of the soft actuator by converting the natural cooling dependent operation into the forced cooling dependent operation.

Also, it is possible to solve the problems of the conventional soft actuator, to control expansion and contraction actively, and to operate linearly against external stimuli.

The soft actuator of the invention is also advantageous in improving accuracy and in broadening the field of application by manipulating the string accurately by using the twisted string and the thermoelectric element.

The soft actuator of the invention can be applied to medical robots and micro artificial muscles that utilize microactuators due to its simple structure using the twisted string and the thermoelectric element, and also applicable to military robots and body function-complementary robots due to its excellent hardness and strong moving force.

The actuator of the invention is also advantageous in eliminating other external factors and in accurate controlling by the thermoelectric element since it does not use light or chemicals but use a thermoelectric element that is close to the string.

The actuator of the present invention also can increase the heating and cooling efficiency of the thermoelectric element by disposing the strings on both sides of the thermoelectric element and can reduce the waste heat of the thermoelectric element.

The soft actuator including the driving part and the thermoelectric element part of the present invention can generate bending moment in both directions by repeating heating and cooling quickly and accurately, so that it can be applied as a band driver to the elbow or knee including the joint, suggesting that the actuator of the invention is advantageous in commercialization as a muscle supplementary band to support the muscular strength of aged people and patients who are in weakness of muscular strength.

According to the present invention, the soft actuator can realize not only bending but also tension, compression, and rotation by the driving part including the unit body composed of the homochiral string and the heterochiral string and by using the driving cable in which the driving part is intruded.

The soft actuator of the present invention can be applied to various fields such as a blood vessel moving robot, a driver of a soft robot, and a gripper for gripping an object by being applied without limiting the size.

BRIEF DESCRIPTION OF THE DRAWINGS

The application of the preferred embodiments of the present invention is best understood with reference to the accompanying drawings, wherein:

FIG. 1 illustrates the string having twist.
FIG. 2 illustrates the string having twist and coiling.
FIG. 3 illustrates the behavior of the heterostring.
FIG. 4 illustrates the behavior of the homostring.
FIG. 5 illustrates the soft actuator according to an example of the present invention.
FIG. 6 illustrates the cross-section of FIG. 5 A.
FIG. 7 illustrates the behavior of the soft actuator according to an example of the present invention.
FIG. 8 illustrates the soft actuator according to another example of the present invention.
FIG. 9 illustrates the soft actuator according to another example of the present invention.
FIG. 10 illustrates the soft actuator according to another example of the present invention.
FIG. 11 illustrates the soft actuator according to another example of the present invention.
FIG. 12 illustrates the soft actuator according to another example of the present invention.
FIG. 13 illustrates the cross-section of FIG. 12 B.
FIG. 14 illustrates the cross-section of a region of the soft actuator according to another example of the present invention where the thermoelectric element is disposed.
FIG. 15 illustrates the soft actuator according to another example of the present invention.

FIG. 16 illustrates the soft actuator according to another example of the present invention.

FIG. 17 illustrates the soft actuator according to another example of the present invention.

FIG. 18 illustrates the soft actuator according to an example of the present invention.

FIG. 19 is the perspective view of FIG. 18.

FIG. 20 illustrates the soft actuator according to another example of the present invention.

FIG. 21 illustrates the soft actuator according to another example of the present invention.

FIG. 22 illustrates the soft actuator according to another example of the present invention.

FIG. 23 illustrates the soft actuator according to another example of the present invention.

FIG. 24 illustrates the soft actuator according to an example of the present invention.

FIG. 25 illustrates the unit body according to an example of the present invention.

FIG. 26 illustrates the driving part or the driving surface according to an example of the present invention.

FIG. 27 illustrates the thermoelectric element part according to an example of the present invention.

FIG. 28 illustrates the soft actuator including the string part according to an example of the present invention.

FIG. 29 illustrates the cylindrical band of the soft actuator according to an example of the present invention.

FIG. 30 illustrates the spreaded cylindrical band of the soft actuator according to an example of the present invention.

FIG. 31 is the perspective view of the soft actuator according to an example of the present invention.

FIG. 32 illustrates the unit body constructing a driving part of the soft actuator according to an example of the present invention.

FIG. 33 is a cross-sectional view of the soft actuator according to an example of the present invention.

FIG. 34 illustrates the compression or tension of the soft actuator according to an example of the present invention.

FIG. 35 illustrates the bending of the soft actuator according to an example of the present invention.

FIG. 36 illustrates the rotation of the soft actuator according to an example of the present invention.

DESCRIPTION OF THE PREFERRED EMBODIMENTS

Hereinafter, the present invention is described in detail.

Soft Actuator (100)

The present invention provides a soft actuator comprising a string that is contracted or expanded by heating or cooling; and a thermoelectric element that can heat or cool the string as arranged at least one side of the string.

The soft actuator (100) according to an example of the present invention may contain a thermoelectric element (120) arranged at least one side of the string surfaces.

FIG. 5 illustrates the soft actuator (100) according to an example of the present invention, and FIG. 6 illustrates the cross-section of FIG. 5 A.

As shown in FIGS. 5 and 6, the soft actuator (100) according to an example of the present invention comprises the twisted string (110); and the thermoelectric element (120) arranged at least one side of the string; wherein the string (110) is contracted or expanded according to the change of the direction of current flowing through the thermoelectric element (120).

Previously, the actuator was designed to move the string (length decrease/increase) by heating and then to recover the string back to the original length (length increase/decrease) by natural cooling. Accordingly, there might be non-symmetrical response time of movement by heat and the recovery from the movement by cooling. However, the soft actuator (100) of an example of the present invention comprises the thermoelectric element (120) for the behavior, so that the operation time of the soft actuator can be reduced by heating and cooling the string (110) by modifying the heating surface and the cooling surface to the direction of current flow.

The soft actuator (100) according to an example of the present invention comprises the string (110) either twisted or twisted and coiled, so that it can respond sensitively and quickly to the temperature change reversibly.

When the temperature of the string (110) is raised by the thermoelectric element (120) arranged in the soft actuator (100), the soft actuator (100) is getting torque as the coiled or twisted string structure becomes loosened. When the raised temperature of the string (110) goes down by the thermoelectric element (120) arranged in the soft actuator (100), the coiled or twisted string structure is recovered, resulting in the reverse torque. By this mechanism, the soft actuator (100) can be heated and cooled down actively. Instead of consuming heat energy passively by the soft actuator (100), the heat energy is converted into mechanical energy to cool down the rotary type soft actuator (100).

In the conventional art, the soft actuator is working to move the string by heating (length reduction/increase) and then to recover the string back to the original length (length increase/reduction) by natural cooling. At this time, asymmetry occurs in the behavior time when the soft actuator is heated to move the string and cooled to recover the string back to the original position.

According to an example of the present invention, the soft actuator (100) comprises the thermoelectric element (120) on at least one side of the twisted string (110) for the behavior, so that the string (110) can be heated or cooled down by changing the heating surface and the cooling surface according to the direction change of current flowing through the thermoelectric element (120). That is, the natural cooling system is converted into the forced cooling system, so that the operation response time of the soft actuator (100) can be reduced. For heating/cooling the soft actuator (100), the thermoelectric element (120) is arranged as a moving source. Therefore, the contraction/expansion of the string (110) is achieved by heating/cooling the thermoelectric element (120). As a result, the continuous operation characteristics of the soft actuator (100) using heat can be improved.

Hereinafter, by referring FIGS. 1~4, the string having the twisted structure included in the soft actuator (100) of the present invention is described.

FIG. 1 illustrates the string having twist. In FIG. 1, the string is twisted in a certain direction with showing bended grain.

In an example of the present invention, the string (110) can be selected from the group consisting of such polymers as nylon, shape memory polyurethane, polyethylene, and rubber, but not always limited thereto. If the string is one of those polymers, the soft actuator (100) can maintain the reversible structure wherein the string is untwisted and retwisted even at a high temperature and thereby durability and lifetime would be extended, suggesting that the actuator can be applied in various fields. The string (110) herein provides the reversible rotation movement, meaning once it is transformed by the high temperature or the low temperature, it can be recovered back to the initial twisted form.

The method to make the string (110) being twisted is either to fix one side and to rotate the other or to rotate both sides. The string (110) may have the structure wherein multiple strands are twisted each other. At this time, the string (110) having the twisted structure made by rotating both sides independently to the opposite direction characteristically ends up the structure of chiral Z type or chiral S type.

FIG. 2 illustrates the string (110) having twist and coiling. As shown in FIG. 2, the string may have twist and coiling. The string (110) can have stronger driving force by heating and cooling and can response more accurately and sensitively by having twist and coiling. The method of imparting coiling to the string is not particularly limited.

For example, one side of the string is fixed and the other side of the string is rotated to be coiled, or the string is wound up with a pipe to make the coiling structure.

FIG. 3 illustrates the behavior of the heterostring, and FIG. 4 illustrates the behavior of the homostring.

The string (110) can be twisted to the right or to the left (twist) and then wound up to the right or to the left (coiling). When the string twisted to the left is wound up to the left or when the string twisted to the right is wound up to the right, it is called 'homochiral string'. When the string twisted to the left is wound up to the right or when the string twisted to the right is wound up to the left, it is called 'heterochiral string'.

The homochiral string increases in length when heated by the thermoelectric element (120) and decreases in length when cooled down by the thermoelectric element (120). The heterochiral string shows the opposite action. So, it decreases in length when heated by the thermoelectric element (120) and increases in length when cooled down by the thermoelectric element (120).

So, the direction of movement caused by the thermoelectric element (120) can be regulated by controlling the direction of twist and coiling of the string (110).

The thermoelectric element (120) can be arranged at least on one side of the twisted string (110). The thermoelectric element (120) can be arranged on the string necessary for the control of the movement of the soft actuator (100). As shown in FIG. 5, the thermoelectric element (120) may be formed to surround a part of the surface of the string (110) in a cylindrical shape, or may be formed so as to surround the entire side of the string (110).

The thermoelectric element (120) is one of the energy conversion devices for converting electric energy into heat energy. The thermoelectric element (120) makes the soft actuator (100) take action actively by heating or cooling the surface of the string by changing the direction of flowing current.

The thermoelectric element includes a thermoelectric power generating device using Seebeck effect which is the effect of generating electromotive force by the temperature difference and a cooling device using Peltier effect which is the effect of generating or absorbing heat when current is flowing in but the present invention is not limited thereto.

The thermoelectric element (120) may be formed of a bulk structure in which a thermoelectric material made of N-type and P-type semiconductors is formed on a ceramic substrate such as alumina ($Al_2O_3$), and the N-type thermoelectric material (123) and the P-type thermoelectric material (122) are connected in series to an electrode.

The thermoelectric element (120) comprises the first electrode (121), the N-type thermoelectric material (123) and P-type thermoelectric material (122) formed on the first electrode (121), and the second electrode (124) for the serial connection of the first electrode (121) and the N-type thermoelectric material (123) and the P-type thermoelectric material (122) together.

The actuator can also be composed of the first substrate, the first electrode (121) arranged on the first substrate, the N-type thermoelectric material (123) and the P-type thermoelectric material (122) arranged on the first electrode (121), the second electrode (124) arranged on the N-type thermoelectric material (123) and the P-type thermoelectric material (122), and the second substrate layered on the second electrode (124). At this time, the soft actuator (100) according to an example of the present invention can be prepared by arranging the completed thermoelectric element on the surface of the string.

The thermoelectric element (120) can be prepared by forming the first electrode (121) in a regular pattern on the surface of the twisted string (110) and by forming the N-type thermoelectric material (123) and the P-type thermoelectric material (122) on the top of the first electrode stepwise and lastly by forming the second electrode (124) on the of the same. The second electrode (124) can be formed by contacting the top of the substrate on which the second electrode (124) is formed in a regular pattern. The N-type thermoelectric material (123) and the P-type thermoelectric material (122) can be connected in series by the first electrode (121) and the second electrode (124).

The N-type thermoelectric material (123) and the P-type thermoelectric material (122) are alternately arranged in the first electrode (121) so as to be easily connected in series by the electrodes. The said P-type thermoelectric material (122) can comprise at least one of those compounds, Si, Al, Ca, Na, Ge, Fe, Pb, Sb, Te, Bi, Co, Ce, Sn, Ni, Cu, Na, K, Pt, Ru, Rh, Au, W, Pd, Ti, Ta, Mo, Hf, La, Ir, and Ag. For example, the N-type thermoelectric material (123) can be $Bi_xTe_{1-x}$ and the P-type thermoelectric material (122) can be $Sb_xTe_{1-x}$.

The N-type thermoelectric material (123) and the P-type thermoelectric material (122) can be formed in the form of a thick film having the thickness of a few~hundreds of micrometer (μm).

The first electrode (121) and the second electrode (124) can be formed to electrically connect the N-type thermoelectric material (123) and the P-type thermoelectric material (122) in series. The first electrode (121) and the second electrode (124) can be arranged such that the first electrode (121) is disposed on the surface of the string, all the electrodes can be formed on the thermoelectric material, or all the electrodes can be formed on the bottom of the thermoelectric material.

The first electrode (121) and the second electrode (124) are preferably those metals which have excellent electrical conductivity, which are exemplified by nickel (Ni), aluminum (Al), copper (Cu), platinum (Pt), ruthenium (Ru) (Au), tungsten (W), cobalt (Co), palladium (Pd), titanium (Ti), tantalum (Ta), iron (Fe), molybdenum (Mo), hafnium (Hf), lanthanum Iridium (Ir), and silver (Ag).

The thermoelectric element (120) is arranged on the surface of the string (110) and can be expanded or contracted with the string (110). Also the thermoelectric element has to be able to operate in response to volume expansion, contraction, or bending of the string (110). Thus, the thermoelectric element (120) may have flexibility.

For the flexibility, the first electrode (121), the N-type thermoelectric material (123), and the P-type thermoelectric material (122), and the second electrode (124) can be composed of those materials that have flexibility or include the composition having flexibility.

Particularly, the first electrode (121), the N-type thermoelectric material (123), the P-type thermoelectric material (122), and the second electrode (124) of the thermoelectric element (120) can include a conductive polymer. The first electrode (121) and the second electrode (124) are formed in the form of nanowires, so that electrical shorting may not occur even when the thermoelectric element is expanded and contracted corresponding to the expansion or contraction of the strings. In addition, the first electrode (121), the N-type thermoelectric material (123), the P-type thermoelectric material, and the second electrode (124) of the thermoelectric element (120) may have a shape including pores therein to cope with the expansion or contraction of the string.

The N-type thermoelectric material (123) can include a bismuth-tellurium (BixTe1-x) compound, and the P-type thermoelectric material (122) can include an antimony-tellurium (SbxTe1-x) compound.

At this time, the conductive polymer included in the first electrode (121), the N-type thermoelectric material (123), the P-type thermoelectric material (122), and the second electrode (124) can be organic conducting polymers such as Poly(3,4-ethylenedioxythiophene):poly(styrenesulfonate) (PEDOT:PSS), Poly(fluorene)s, Polyphenylenes, Polypyrenes, Polyazulenes, Polynaphthalenes, Poly(acetylene)s (PAC), Poly(p-phenylene vinylene) (PPV), Poly(pyrrole)s (PPY), Polycarbazoles, Polyindoles, Polyazepines, Polyanilines (PANI), Poly(thiophene)s (PT), Poly(3,4-ethylenedioxythiophene) (PEDOT), and Poly(p-phenylene sulfide) (PPS) and might include organic non-conducting polymers such as Polydimethylsiloxane (PDMS), Poly(methylmethacrylate), Poly(p-phenylene terephthalamide), and Polyethylene.

The substrate included in the thermoelectric element (120) can be a flexible substrate so that the thermoelectric element (120) can have flexibility. The flexible substrate is to support the whole thermoelectric element and at the same time to give flexibility to the thermoelectric element, which is exemplified by a polyimide film, a Kapton film, a polyester film, a PEN film, a plastic film, PDMS, and paper, but not always limited thereto. It is preferable that the flexible substrate is made of a material having heat resistance enough to withstand the subsequent process temperature.

The first electrode (121), the N-type thermoelectric material (123), the P-type thermoelectric material (122), and the second electrode (124) of the thermoelectric element (120) can include a conductive polymer. The conductive polymer can include poly-3,4-ethylenedioxythiophene/polystyrenesulfonate (PEDOT/PSS), polyaniline, polyacetylene or polyphenylene vinylene, but not always limited thereto.

The first electrode (121) and the second electrode (124) are formed in the form of nanowires, so that electrical shorting may not occur even when the thermoelectric element is expanded and contracted corresponding to the expansion or contraction of the string. In addition, the first electrode (121), the N-type thermoelectric material (123), the P-type thermoelectric material, and the second electrode (124) of the thermoelectric element (120) may have a shape including pores therein to cope with the expansion or contraction of the string.

The N-type thermoelectric material (123) and the P-type thermoelectric material (122) are alternately arranged on the first electrode (121) and connected in series by the first electrode (121).

Herein, the N-type thermoelectric material (123) and the P-type thermoelectric material (122) include pores therein, and at least some of those pores are filled with organic polymer materials.

FIG. 7 illustrates the behavior of the soft actuator (100) according to an example of the present invention. As shown in FIG. 7, the soft actuator (100) of the present invention can be expanded and contracted by supplying current to the thermoelectric element (120) arranged on the surface of the string (110). So, the operation response time of the soft actuator (100) can be reduced by converting the natural cooling dependent operation into the forced cooling dependent operation.

FIG. 8 illustrates the soft actuator (200) according to another example of the present invention.

As shown in FIG. 8, the soft actuator (200) of the invention can additionally include the control unit (230) to control the direction of current flowing through the thermoelectric element (220).

The control unit (230) can change the direction of current flowing through the thermoelectric element (220), by which the temperature of the surface of the string can be raised or lowered (heating or cooling) to make the soft actuator (200) operate actively.

FIG. 9 illustrates the soft actuator (300) according to another example of the present invention.

As shown in FIG. 9, the soft actuator includes the adhesive layer (340) to connect the string (310) and the thermoelectric element (320). The adhesive layer (340) can be disposed between the thermoelectric element (320) and the string (310), which plays a role of adhering the first electrode of the thermoelectric element (320) onto the surface of the string (310). When the substrate is included in the thermoelectric element (320), the substrate can be contacted with the surface of the string (310). The adhesive layer (340) can include metal epoxy, for example silver (Ag) epoxy. The adhesive layer (340) may be an adhesive, yet have a high electrical conductivity, and may have a suitable viscosity to allow deformation when appropriate pressure is applied.

The adhesive layer (340) can include a binder, which is exemplified by a thermoplastic resin. The thermoplastic resin herein can be selected from the group consisting of acrylonitrile resin, phenoxy resin, butadiene resin, acrylic resin, urethane resin, polyamide resin, olefin resin, string-reinforced resin, and NBR (nitrile butadiene rubber) resin, but not always limited thereto. The binder used for the adhesive layer (340) can be the binder resin not comprising an epoxy group. The thermoplastic resin preferably has a weight average molecular weight of 1,000~1,000,000 g/mol. Within the above range, it is possible to have proper film strength, to prevent phase separation, and to adhere to the conductive layer or the non-conductive layer, so that the adhesive strength is not lowered. The preferable concentration of the binder in the adhesive layer (340) is 20~70 weight % by the weight of the solid component. The concentration in that range favors the film formation.

The adhesive layer (340) can additionally include hydrophobic string rica and/or other additives, if necessary. In that case, the preferable amount of the additionally included additive is 1~10 weight % by the weight of the solid component.

FIG. 10 illustrates the soft actuator (400) according to another example of the present invention.

As described hereinbefore, the string included in the soft actuator (400) according to an example of the present invention has the structure of twist and coiling. At this time, the thermoelectric element (420) arranged on the string (410) can be formed before the coiling process. As shown in FIG. 10, the thermoelectric element (420) can be formed to wrap the side of the string (410). Before the coiling process of the string (410), deposition process or adhesion process can be performed to form the thermoelectric element (420). At this time, the string (410) and the thermoelectric element (420) of the soft actuator (400) can contact with each other on a large surface, so that the soft actuator (400) can be operated more accurately and faster, and higher power can be obtained.

FIG. 11 illustrates the soft actuator (500) according to another example of the present invention.

According to FIG. 11, when the thermoelectric element (520) is formed on the coiled string (510), the thermoelectric element might not be arranged in the inside of the coiling area or in the region where the strings contact with each other during the deposition process or adhesion process. Through this process, it is possible to prevent breakage of the thermoelectric element that may occur due to the process of imparting coiling to the string.

FIG. 12 illustrates the soft actuator (600) according to another example of the present invention and FIG. 13 illustrates the cross-section of FIG. 12 B.

As shown in FIGS. 12 and 13, the soft actuator (600) according to an example of the present invention includes the twisted string (610) and the thermoelectric element (620) arranged on at least one side of the string (610).

The actuator can be operated by heating or cooling the surface of the string (610) by converting the direction of current flowing through the thermoelectric element (620) arranged on both ends of the string. By that system, the symmetrical response to the contraction/expansion of the soft actuator (600) can be configured to improve the operating characteristics and increase the usability of the soft actuator (600).

Conventionally, heat is applied to move the string (length reduction/increase) and return to its original position (length increase/reduction) by natural cooling. At this time, there might be asymmetrical difference between the time for driving by heat and the time driving by cooling. In an example of the present invention, the thermoelectric element for driving is arranged in the soft actuator and the heating surface and the cooling surface of the thermoelectric element can be converted by changing the direction of current flowing therein, suggesting that the operating response time of the soft actuator can be reduced by heating or cooling the string.

When the temperature of the string (610) of the soft actuator (600) is raised by the thermoelectric element (620) arranged on one side of the string, the twisted or coiled structure of the soft actuator (600) becomes loose, by which the actuator gains the rotational force. When the temperature of the string (610) of the soft actuator (600) is lowered by the thermoelectric element (620), the loosened structure is recovered back to the original coiled or twisted structure, during which the rotational force in the opposite direction is generated.

The string (610) herein can be selected from the group consisting of such polymers as nylon, shape memory polyurethane, polyethylene, and rubber, but not always limited thereto. When a polymer is used as the string, the soft actuator (100) can maintain its reversible structure between untwist and retwist for a long time even at a high temperature and also maintain durability and longer life time, so that it can be applied to various fields. The string (610) provides a reversible rotational movement back to the initial twisted form even if the shape is deformed by high or low temperature.

The string (610) can be the string described in the example explained hereinbefore.

The thermoelectric element (620) can be the one described in another the example described hereinbefore, but not always limited thereto.

FIG. 14 illustrates the cross-section of a region of the soft actuator (600) according to another example of the present invention where the thermoelectric element (620) is disposed. As shown in FIG. 14, the multiple thermoelectric elements (620) can be arranged in the layered structure in order to apply sufficient heat to the string (610). At this time, the first electrode (721a) is disposed on the cross-section of the string (610), and the N-type thermoelectric material (723a) and the P-type thermoelectric material (722a) are disposed on the first electrode (721a). Then, the second electrode (724a) is arranged on the N-type thermoelectric material (723a) and the P-type thermoelectric material (722a). After placing the first thermoelectric element in this way, the second thermoelectric element can be placed across the insulating layer (750). The first electrode (721b) can be arranged on the insulating layer (750) and the N-type thermoelectric material (723b) and the P-type thermoelectric material (722b) can be arranged on the first electrode (721b) and then the second electrode (724b) can be placed on the N-type thermoelectric material (723b) and the P-type thermoelectric material (722b). The first thermoelectric element and the second thermoelectric element may be connected in series by wires. By arranging the same heating surface and cooling face toward the cross-section of the string, the movement of the soft actuator (600) can be more accurately controlled and the power can be strengthened.

FIG. 15 illustrates the soft actuator (600) according to another example of the present invention.

The thermoelectric element allows the actuation of the soft actuator (600) by heating or cooling the surface of the string by changing the current direction. The control unit (830) can be connected to the thermoelectric element by a wire, by which the movement thereof can be controlled.

FIG. 16 illustrates the soft actuator (600) according to another example of the present invention. As shown in FIG. 16, in the soft actuator (600) according to another example of the present invention, the string and the thermoelectric element are connected with each other by the adhesive layer (940) arranged in between the cross-section of the string (610) and the thermoelectric element (620). The adhesive layer (940) can include metal epoxy, for example silver (Ag) epoxy. The adhesive layer (940) may be an adhesive, yet have a high electrical conductivity, and may have a suitable viscosity to allow deformation when appropriate pressure is applied.

FIG. 17 illustrates the soft actuator (1000) according to another example of the present invention.

As shown in FIG. 17, the string (1010) may have twist and coiling. The string (1010) can have stronger driving force by heating and cooling and can response more accurately and sensitively by having twist and coiling. The method of imparting coiling to the string is not particularly limited. For example, one side of the string is fixed and processed while the other side of the string is rotating, resulting in the coiling structure. Or, the coiling structure can be produced by wrapping a pipe with the string.

The soft actuator (100) according to an example of the present invention can include the first string and the second string and the thermoelectric element can be arranged between the first string and the second string.

FIG. 18 illustrates the soft actuator (100) according to an example of the present invention and FIG. 19 is the perspective view of FIG. 18.

As shown in FIGS. 18 and 19, the soft actuator (100) according to an example of the present invention comprises the twisted first string (111) and the second string (121), and the thermoelectric element (120) arranged between the first string (111) and the second string (131).

Conventionally, heat is applied to move the string (length reduction/increase) and return to its original position (length increase/reduction) by natural cooling. At this time, there might be asymmetrical difference between the time for driving by heat and the time driving by cooling.

In an example of the present invention, the thermoelectric element (120) for driving is arranged in the soft actuator (100) and the heating surface and the cooling surface of the thermoelectric element (120) can be converted by changing the direction of current flowing therein, suggesting that the operating response time of the soft actuator (100) can be reduced by heating or cooling the first string (111) and the second string (131).

The soft actuator (100) according to an example of the present invention comprises the first string (111) and the second string (131) either twisted or twisted and coiled, so that it can respond sensitively and quickly to the temperature change reversibly.

The thermoelectric element (120) above can increase the heating or cooling efficiency by contacting physically with the first string (111) and the second string (131). In addition, the thermoelectric element is physically spaced apart from the first string and the second string to prevent the physical force from being transmitted to the thermoelectric element as the first string and the second string are expanded or relaxed.

When the temperature of the first string (111) and the second string (131) is raised by the thermoelectric element (120) arranged in the soft actuator (100), the soft actuator (100) is getting torque as the coiled or twisted structure of the first string (111) and the second string (131) becomes loosened. When the raised temperature of the first string (111) and the second string (131) goes down by the thermoelectric element (120) arranged in the soft actuator (100), the coiled or twisted structure is recovered, resulting in the reverse torque. By this mechanism, the soft actuator (100) can be heated and cooled down actively. Instead of consuming heat energy passively by the soft actuator (100), the heat energy is converted into mechanical energy to cool down the rotary type soft actuator (100).

FIG. 20 illustrates the soft actuator (200) according to another example of the present invention. As shown in FIG. 20, the soft actuator (200) of the invention can additionally include the control unit (230) to control the direction of current flowing through the thermoelectric element (220).

The control unit (230) can change the direction of current flowing through the thermoelectric element (220), by which the temperature of the surface of the first string (211) and the second string (231) can be raised or lowered (heating or cooling) to make the soft actuator (200) operate actively.

FIG. 21 illustrates the soft actuator (300) according to another example of the present invention. As shown in FIG. 21, in the soft actuator (300) of the present invention, the thermoelectric element (320) may be disposed between the first string (311) and the second string (331) in a three-dimensional shape corresponding to the first string (311) and the second string (331). Although the thermoelectric element (320) has a narrow area as compared with the plate type, the area contributing to heating or cooling the first string (311) and the second string (331) can be sufficiently large. Therefore, the production cost can be reduced by disposing the thermoelectric element (320) in a zigzag shape as shown in FIG. 21, or arranging the thermoelectric element (320) in parallel with the side way of the first string (311) or the second string (331). When the first string (311) or the second string (331) is expanded or contracted, the thermoelectric element (320) can respond more easily to the movement of the first string (311) or the second string (331).

The thermoelectric element (320) can contact physically with the first string (311) or the second string (331). The thermoelectric element can be arranged between the first string and the second string with maintaining distance from them. The thermoelectric element (320) can be the same as explained in another example hereinbefore, but not always limited thereto.

FIG. 22 illustrates the soft actuator (400) according to another example of the present invention. As explained hereinbefore, the first string (411) and the second string (431) included in the soft actuator (400) according to an example of the present invention can have the structure of twist and coiling.

At this time, the thermoelectric element (420) arranged in between the first string (411) and the second string (431) can be formed before the coiling process. That is, after the thermoelectric element (420) is arranged between the first string (411) and the second string (431), coiling can be imparted to the bundle of the first string (411), the thermoelectric element (420), and the second string.

Alternatively, the soft actuator can be prepared in which the first string (411), the second string (431), and the thermoelectric element (420) are coiled and then the first string (411), the second string (431), and the thermoelectric element (420) are assembled.

The thermoelectric element (420) disposed between the first string (411) and the second string (431) can be placed horizontally to the main driving axle of the soft actuator (400). The main behavior of the soft actuator (400) is longitudinal motion of the actuator, whether elongated or contracted in the longitudinal direction.

As shown in FIG. 22, the first string (411), the thermoelectric element (420), and the second string (431) are arranged vertically to the direction of coiling. So, the first string (411) is heated or cooled according to the heating or cooling of one side of the thermoelectric element (420), and the second string (431) is cooled or heated according to the cooling or heating of the other side of the thermoelectric element (420). That is, the first string (411) and the second string (431) can perform the positive and reverse reactions simultaneously, suggesting that the soft actuator (400) can increase the efficiency in power and operating time.

The first electrode and the second electrode of the thermoelectric element (420) are directly or indirectly connected to the first string (411) and the second string (431), and the P-type thermoelectric material and the N-type thermoelectric material are arranged by turns in between the first electrode and the second electrode. The thermoelectric element (420) can be connected to the first string (411) and the second string (431) by the adhesive layer. The thermoelectric element (420) above can be the same as the one described in another example of the invention, but not always limited thereto.

FIG. 23 illustrates the soft actuator (500) according to another example of the present invention. As explained hereinbefore, the first string (511) and the second string (531) included in the soft actuator (500) according to an example of the present invention can have the structure of twist and coiling.

At this time, the thermoelectric element (520) arranged in between the first string (511) and the second string (531) can be formed before the coiling process. That is, after the thermoelectric element (520) is arranged between the first string (511) and the second string (531), coiling can be imparted to the bundle of the first string (511), the thermoelectric element (520), and the second string (531).

Alternatively, the soft actuator can be prepared in which the first string (511), the second string (531), and the thermoelectric element (520) are coiled and then the first string (511), the second string (531), and the thermoelectric element (520) are assembled.

The thermoelectric element (520) disposed between the first string (511) and the second string (531) can be placed horizontally to the main driving axle of the soft actuator (500). The main behavior of the soft actuator (500) is longitudinal motion of the actuator, whether elongated or contracted in the longitudinal direction.

As shown in FIG. 23, the first string (511), the thermoelectric element (520), and the second string (531) are arranged horizontally to the direction of coiling. So, the first string (511) is heated or cooled according to the heating or cooling of one side of the thermoelectric element (520), and the second string (531) is cooled or heated according to the cooling or heating of the other side of the thermoelectric element (520). That is, the first string (511) and the second string (531) can perform the positive and reverse reactions simultaneously, suggesting that the soft actuator (500) can increase the efficiency in power and operating time.

The first electrode and the second electrode of the thermoelectric element (520) are directly or indirectly connected to the first string (511) and the second string (531), and the P-type thermoelectric material and the N-type thermoelectric material are arranged by turns in between the first electrode and the second electrode. The thermoelectric element (520) can be connected to the first string (511) and the second string (531) by the adhesive layer. The thermoelectric element (520) above can be the same as the one described in another example of the invention, but not always limited thereto.

Further, the present invention provides a soft actuator comprising:

a driving part as one unit comprising the first string that can be expanded or contracted by heating or cooling, the second string that can move oppositely to the first string by heating or cooling, wherein the first string and the second string are not contacted with each other; and a thermoelectric element part to heat or cool the driving part.

At this time, the thermoelectric element part is arranged with the driving part so that the area where the conductor is formed can heat or cool the first string and the second string.

(Patent 5)

FIG. 24 illustrates the soft actuator (1) according to an example of the present invention.

The soft actuator (1) according to an example of the present invention can include a driving part (11), a thermoelectric element part (13), a power supply part (15), and a string part (17, FIG. 29).

The soft actuator (1) comprises a driving part (11) composed of the first string (1101) that can be contracted or expanded by heating or cooling and the second string (1103) that moves against the first string by heating or cooling wherein the strings are arranged not to be contacted with each other while both making one unit; and a thermoelectric element part (13) that heats or cools the driving part (11), in which a conductor region (133) is arranged against the driving part (11) in order to heat or cool the first string (1101) and the second string (1103).

As shown in FIG. 24, the soft actuator (1) according to an example of the present invention might not include the string part (17, FIG. 28). The soft actuator (1) can have the first string (1101) and the second string (1103) arranged by turns. The first string (1101) or the second string (1103) of the soft actuator (1) can be either homochiral or heterochiral fiber or both. The first string (1101) and the second string (1103) can be different strings in different structures. In the soft actuator (1), the first string (1101) and the second string (1103) can construct one unit (1100). In the soft actuator (1), the unit (1100) can be connected in parallel. The thermoelectric element part (13) can be arranged by crossing over the unit (1100) connected in parallel in the soft actuator (1).

The soft actuator (1) can additionally include the power supply part (15) to form a closed circuit with the thermoelectric element part (13) and to provide current to the thermoelectric element part (13).

In an example of the present invention, the soft actuator (1) can be connected in series with the power supply part (15) and the thermoelectric element part (13). The soft actuator (1) can generate heat energy by flowing current through the thermoelectric element part (13) connected in series to the power supply part (15). The soft actuator (1) can transmit the heat energy generated in the thermoelectric element part (13) to the driving part (11). The driving part (11) provided the heat energy generates bending moment in the soft actuator (1), by which the soft actuator (1) can drive.

The soft actuator (1) can additionally include the string part (17, FIG. 28) composed of flexible strings connected in parallel to the side of the unit (1100).

As shown in FIG. 28, the soft actuator (1) according to an example of the invention can additionally include the string part (17) to support the movement of the driving part (11). The soft actuator (1) shown in FIG. 28 is described in more detail in the following example 1.

The soft actuator (1) can have the structure wherein the thermoelectric element part (13) is crossing over the top side or the bottom side of the first string (1101) and the second string (1103) and the first string (1101) and the second string (1103) are arranged in the opposite side.

In an example of the present invention, in the soft actuator (1), the driving part (11) and the thermoelectric element part (13) can be arranged in various forms. For example, the driving part (11) is arranged on top side of the thermoelectric element part (13) in the soft actuator (1). Or the driving part (11) can be arranged on the bottom side of the thermoelectric element part (13) in the soft actuator (1). In particular, the driving part (11) and the thermoelectric element part (13) can cross over each other in the soft actuator (1). At this time, the driving part (11) and the thermoelectric element part (13) can be connected tightly with each other due to the structural characteristics of the soft actuator (1).

FIG. 1 illustrates the twisted structure of the string constructing the driving part (11) of the soft actuator (1) according to an example of the present invention.

The string that can compose the driving part (11) of the soft actuator (1) according to an example of the present invention can be the first string (1101) or the second string (1103). The string composing the driving part (11) of the soft actuator (1) can be homostring or heterostring. The string constituting the driving part (11) of the soft actuator (1) can be selected from the group consisting of such polymers as nylon, shape memory polyurethane, polyethylene, and rubber. By using such polymers as the string forming the soft actuator (1), the soft actuator (1) can maintain the reversible structure wherein the string is untwisted and retwisted even at a high temperature. The string forming the soft actuator (1) can be changed not only by heating but also by cooling, so that it can provide a reversible rotation movement to going back to the initial coiled structure.

As shown in FIG. 1, the string forming the driving part (11) of the soft actuator (1) according to an example of the present invention is primarily twisted. To give the twisted structure to the string forming the driving part (11) of the soft actuator (1), one end of the string is fixed and the other end of the string is rotated or both ends are rotated.

FIG. 2 illustrates the coiling structure of the string constructing the driving part (11) of the soft actuator (1) according to an example of the present invention.

As shown in FIG. 2, the string forming the driving part (11) of the soft actuator (1) can be twisted first and then the twisted string can be coiled additionally. A method to make the string forming the driving part (11) of the soft actuator (1) coiled is not limited to a specific one. As an example, one side of the string is fixed and the other side of the string is rotated to make the coiling structure. Or, the string wraps a pipe to make the string coiled. When the string is twisted and coiled at the same time, the driving force of the string induced by heating and cooling becomes strong and the characteristics of the string can be changed according to the direction of the twist and coiling.

FIG. 4 illustrates the homochiral string forming the driving part (11) of the soft actuator (1) according to an example of the present invention. As shown in FIG. 2, the homochiral string is the string in which the directions of both twist and coiling are same. The homochiral string can be contracted as the string is heated by the thermoelectric element part (13) and can be expanded as the string is cooled by the thermoelectric element part (13).

FIG. 3 illustrates the heterochiral string forming the driving part (11) of the soft actuator (1) according to an example of the present invention. As shown in FIG. 3, the heterochiral string is the string in which the direction of twist is opposite to the direction of coiling. The heterochiral string can move oppositely to the homochiral string. The heterochiral string can be expanded as the string is heated by the thermoelectric element part (13) and can be contracted as the string is cooled by the thermoelectric element part (13).

In an example of the present invention, the direction of contraction and expansion of the homochiral or heterochiral string is not limited to the longitudinal direction of the string. The homochiral string can be called the first string (1101) or the second string (1103), and the heterochiral string can be called the first string (1101) or the second string (1103) that is not the homochiral string. When the first string (1101) and the second string (1103) are arranged one by one with maintaining some distance between them, it is called the unit body (1100).

FIG. 25 illustrates the unit body (1101) according to an example of the present invention.

As shown in FIG. 25, the driving part (11) realizes a single drive of the unit body (1100) by cooling one of the strings, the first string (1101) and the second string (1103), and heating the other string by the heat energy delivered from the thermoelectric element part (13).

In an example of the present invention, the unit body (1100) is composed of the first string (1101) and the second string (1103) contracted or expanded to the opposite direction according to heating or cooling which are arranged with maintaining some distance. The unit body (1100) composed of those first string (1101) and second string (1103) realizes the same movement, either contraction or expansion, between the first string (1101) and the second string (1103) even when they are separately treated with heating or cooling, and thereby the unit body (1100) realizes a single driving when current is applied through the thermoelectric element part (13).

FIG. 26 illustrates the driving part (11) or the driving surface (11a or 11b) according to an example of the present invention.

In an example of the present invention, the unit body (1100) is connected to the thermoelectric element part (13) to receive heat energy. The unit body (1100) can receive different types of heat energy as current flows through the thermoelectric element part (13). For example, the first string (1101) can be heated by the thermoelectric element part (13) and the second string (1103) can be cooled by the thermoelectric element part (13). Or reversely, the first string (1101) can be cooled by the thermoelectric element part (13) and the second string (1103) can be heated by the thermoelectric element part (13). Accordingly, those two strings, the first string (1101) and the second string (1103) showing different behaviors according to the heat energy type can move to the same direction.

The driving part (11) may have a plurality of the unit bodies (1100) arranged in parallel.

In an example of the present invention, the driving part (11) can have the structure comprising multiple unit bodies (1100). For example, the driving part (11) is composed of multiple unit bodies (1100) arranged in parallel.

The first fiber (1101) and the second fiber (1103) of the unit body (1100) forming the driving part (11) can receive different types of heat energy from the thermoelectric element part (13) to implement the same operation. Therefore, in the driving part (11) having various shapes, the conductive body of the thermoelectric element part (13) should be set in a proper arrangement in consideration of the operation direction. The operation direction of the driving part (11) and the setting of the thermoelectric element part (13) are described in more detail in the following example illustrated by FIG. 27.

FIG. 27 illustrates the thermoelectric element part (13) according to an example of the present invention.

In an example of the present invention, the thermoelectric element part (13) indicates the device using thermoelectric effect.

Thermoelectric effect is the general term for the three heat and electric correlation phenomena including Seebeck effect, Peltier effect, and Thomson effect. The thermoelectric element part (13) according to an example of the present invention uses Peltier effect among those thermoelectric effects.

Peltier effect is understood as the phenomenon that when current is flowing in a metal, heat is flowing together therein and at that time heat seems to be generated or absorbed on the connection surface due to the difference in heat flow between two metals. The heat generation and absorption in Peltier effect is reversible. When one side generates heat by current flow, the other side absorbs the heat. When the direction of current flow is changed, the heat generation turns to the absorption and the heat absorption changes into the heat generation. In particular, in Peltier effect, when the current value is increased and the conductor material and combination are appropriately selected so that cooling system is working by endotherm of the contact point, which is called thermoelectric cooling. The thermoelectric cooling phenomenon is currently used in the temperature range of a freezer, but a method of multi-stage cooling to 70K is also being developed.

As shown in FIG. 27, the thermoelectric element part (13) can include the first conductive body (132), the second conductive body (135) showing different direction of heat flow from the first conductive body (132), and the conductor (133) arranged in series between the first conductive body (132) and the second conductive body (135).

In an example of the present invention, the thermoelectric element part (13) is composed of the first conductive body (132), the second conductive body (135), and the conductor (133). In the thermoelectric element part (13), the first conductive body (132), the second conductive body (135), and the conductor (133) are arranged in series, so that the current delivered from the power supply part (15) can be converted into heat energy which is then delivered to the driving part (11). The first conductive body (132) of the thermoelectric element part (13) can be n-type semiconductor or p-type semiconductor, and the second conductive body (135) of the thermoelectric element part (13) can be different type of semiconductor from the first conductive body (132) in the thermoelectric element part (13). The conductor, n-type semiconductor and p-type semiconductor will be described hereinafter.

The conductor (133) is a material having a high electrical conductivity and a high thermal conductivity. That is, it is a material that delivers electricity and heat well. The conductor (133) refers to the corresponding term of the insulator. Such metals as gold, silver, and copper are the typical conductor (133) delivering electricity and heat. Conductors conducting electricity can be classified as solid conductors and liquid conductors. In particular, the representative solid conductor is metal and the representative liquid conductor is aqueous solution of acid, alkali, and salt.

In general, when free electrons are plenty in a semiconductor, it is called n-type semiconductor. On the contrary, when hole density is bigger than free electron density, it is classified as p-type semiconductor. The ionized impurity atom that lost electrons is called a donor. When the impurity is the donor, it is n-type semiconductor. In p-type semiconductor, current is flowing by an acceptor. P-n-p transistor, n-p-n transistor, or p-n-p-n device can be prepared by combining the p-type and the n-type semiconductors. The semiconductor diode is the most basic p-n complex.

The thermoelectric element part (13) can heat or cool the conductor (133) by the divided pathways, which are the conduction pathway through which current is delivered to the second conductive body (135) via the conductor (133) after passing through the first conductive body (132); and the other conduction pathway through which current is delivered to the first conductive body (132) via the conductor (133) after passing through the second conductive body (135).

In an example of the present invention, the first conductive body (132), the second conductive body (135), and the conductor (133) are arranged in series in the thermoelectric element part (13), by which current is provided from the power supply part (15). The first conductive body (132) or the second conductive body (135) of the thermoelectric element part (13) can be connected to the power supply part. The thermoelectric element part (13) can heat or cool the conductor (133) according to the direction of current supplied to the first conductive body (132) and the second conductive body (135).

The driving part (11) can realize a single drive of the unit body (1100) by shrinking or expanding the first string (1101) and the second string (1103) together as the conductor (133) is heated or cooled.

When current passing through the n-type semiconductor and flowing through the conductor (133) to the p-type semiconductor is supplied in the thermoelectric element part (13), the conductor (133) can be cooled. On the other hand, when current is flowing from the p-type semiconductor and passing through the conductor (133) and then heading to the n-type semiconductor, the conductor (133) can be heated. The cooled or heated conductor (133) can deliver heat energy to cool or heat the driving part (11).

In an example of the present invention, the power supply part (15) can form a closed circuit with the thermoelectric element part (13). The power supply part (15) can supply current to the thermoelectric element part (13). The power supply part (15) selects the direction of current and transmits energy in the direction of shrinking or expanding the driving part (11). The power supply part (15) can comprise any configuration that may be installed in the driving part (11), installed in the string part (17, FIG. 28), or installed outside the soft actuator (1) to provide current.

<Example 1> Soft Actuator (1) Comprising the String Part (17)

FIG. 28 illustrates the soft actuator (1) including the string part (17) according to an example of the present invention.

The soft actuator (1) according to an example of the present invention can have the string part (17) connected in parallel to the side of the driving part (11) wherein the unit body (1100) is arranged in parallel. The soft actuator (1) can also have the power supply part (15) attached to the string part (17). In the soft actuator (1), the thermoelectric element part (13) and the power supply part (15) can make a closed circuit. In the soft actuator (1), the thermoelectric element part (13) and the driving part (11) cross each other several times. The soft actuator (1) can be set to supply same heat energy to one of the first string (1101) and the second string (1103). The soft actuator (1) can include the unit body (1100) and the driving part (11) driving to the same direction. In the soft actuator (1), the string part (17) can support the driving of the driving part (11). The string part (17) of the soft actuator (1) can be made of a flexible material. In FIG. 28, it is shown that some of the conductor (133) are installed outside the string part (17), however the soft actuator (1) can have the structure wherein the conductor (133) having a wide area and the string part (17) are connected. In the soft actuator (1), the power supply part (15) determines the direction of current flow, so that the direction of contraction or expansion of the driving part (11) can be regulated. The soft actuator (1) having the single driving part (11) prepared in a detachable form on the body can be used as a muscular strength aid to assist muscular strength.

<Example 2> Cylindrical Soft Actuator (1)

FIG. 29 illustrates the cylindrical band of the soft actuator (1) according to an example of the present invention.

FIG. 30 illustrates the spreaded cylindrical band of the soft actuator (1) according to an example of the present invention.

In the soft actuator, the multiple unit bodies (1100) are arranged in parallel to form the driving surface (11*a* or 11*b*) and the driving surface (11*a* or 11*b*) makes a pair with the string part (17) composed of the flexible string connected to the side of the unit body (1100) in parallel, and these pairs are arranged by turns to form the cylindrical side wall. In the thermoelectric element part (13), a conduction pathway is formed on the one driving surface (11a or 11b) in which current is transmitted to the second conductive body (135) through the conductor (133) via the first conductive body (132), and another conduction pathway is formed on the other driving surface (11a or 11b) in which current is transmitted to the first conductive body (132) through the conductor (133) via the second conductive body (135). This pair of driving surfaces (11a and 11b) can generate a bending moment by realizing different drivings during contraction or expansion when it is supplied with current from the thermoelectric element part (13).

In an example of the present invention, the soft actuator (1) can be prepared in the form of a cylinder including hollows. By comprising the driving part (11) and the string part (17), the soft actuator (1) exhibits the characteristics of a flexible band. By the parallel connection of the unit body (1100) in the soft actuator (1), the width of the driving surface (11a or 11b) can be changed. The driving surface (11a or 11b) of the soft actuator (1) can be divided into the first driving surface (11a) and the second driving surface (11b) that can be contracted or expanded differently when current is supplied from the power supply part (15). In the soft actuator (1), the thermoelectric element part (13) and the power supply part (15) can form a closed circuit. In the soft actuator (1), the power supply part (15) can be placed in the string part (17). In the first driving surface (11a) and the second driving surface (11b) of the soft actuator (1), n-type semiconductor or p-type semiconductor is arranged differently, so that the first driving surface (11a) and the second driving surface (11b) can be contracted or expanded by the direction of current.

As shown in FIG. 30, the driving surface (11a or 11b) is supplied with current in the other direction from the power supply part (15) to realize two kinds of bending moments. The power supply part (15) can supply current to the right or to the left. Therefore, when current is supplied from the power supply part (15) to the driving surface (11a or 11b) to the direction of right, the first driving surface (11a) is expanded, and therefore the second driving surface (11b) is contracted. On the other hand, when current is supplied from the power supply part (15) to the driving surface (11a or 11b) to the direction of left, the first driving surface (11a) is contracted and therefore the second driving surface (11b) is expanded. The opposite driving between the first driving surface (11a) and the second driving surface (11b) can generate a bending moment in the cylindrical soft actuator (1). The cylindrical soft actuator (1) that can generate a bending moment can be used as a muscular strength aid to support muscular strength by being worn on some body parts with joints, such as elbows or knees. In particular, the cylindrical soft actuator (1) can assist in fast and repetitive motion, such as climbing stairs when worn on a user's knee.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

FIG. 31 is the perspective view of the soft actuator according to an example of the present invention.

As shown in FIG. 31, the soft actuator (1) can include the driving part (11) and the driving cable (13).

The soft actuator (1) can include the driving part (11) composed of the unit body (1100) comprising the first string (1101) which is twisted and coiled and the second string (1103) which is also twisted and coiled and placed with maintaining some distance from the first string (1101); and the driving cable (12) in which a hollow is formed and the unit body (1100) is inserted into the hollow.

In an example of the present invention, in the driving part (11) of the soft actuator (1), the first string (1101) has a smaller coiling radius than the second string (1103) and the second string (1103) wraps the first string (1101) to form the unit body (1100). In the soft actuator (1), the driving part (11) can be introduced into the driving cable (12) to implement the driving of the soft actuator (1).

FIG. 31 illustrates the twisted string that forms the driving part (11) of the soft actuator (1) according to an example of the present invention.

As shown in FIG. 31, the string forming the driving part (11) of the soft actuator (1) of the invention is primarily twisted. To give the twisted structure to the string forming the driving part (11) of the soft actuator (1), one end of the string is fixed and the other end of the string is rotated or both ends are rotated. The direction of the twisting in the string forming the driving part (11) of the soft actuator (1) itself does not affect the driving of the soft actuator (1), and instead the relation between the coiling direction and twist direction which will be described hereinafter can determine the characteristics of the string. The diameter and the size of the string forming the driving part (11) of the soft actuator (1) are not limited and can be different between the first string (1101) and the second string (1103).

In an example of the present invention, the string constituting the driving part (11) of the soft actuator (1) can be selected from the group consisting of such polymers as nylon, shape memory polyurethane, polyethylene, and rubber. By using such polymers as the string forming the soft actuator (1), the soft actuator (1) can maintain the reversible structure wherein the string is untwisted and retwisted even at a high temperature. The string forming the soft actuator (1) can be changed not only by heating but also by cooling, so that it can provide a reversible rotation movement to going back to the initial coiled structure.

FIG. 1 illustrates the coiling structure of the string constructing the driving part (11) of the soft actuator (1) according to an example of the present invention.

As shown in FIG. 1, the string forming the driving part (11) of the soft actuator (1) can be twisted first and then the twisted string can be coiled additionally. The direction of coiling of the string forming the driving part (11) of the soft actuator (1) can be equal to or different from the direction of twist. A method to make the string forming the driving part (11) of the soft actuator (1) coiled is not limited to a specific one.

As an example, one side of the string is fixed and the other side of the string is rotated to make the coiling structure. Or, the string wraps a pipe to make the string coiled. When the string is twisted and coiled at the same time, the driving force of the string induced by heating and cooling becomes strong and the characteristics of the string can be changed according to the direction of the twist and coiling. The volume of the string forming the driving part (11) of the soft actuator (1) can be varied from the twist and coiling.

FIG. 4 illustrates the homochiral string forming the driving part (11) of the soft actuator (1) according to an example of the present invention.

The homochiral string is the string in which the directions of both twist and coiling are same. The homochiral string can be contracted as the string is heated and can be expanded as the string is cooled.

FIG. 3 illustrates the heterochiral string forming the driving part (11) of the soft actuator (1) according to an example of the present invention.

The heterochiral string is the string in which the direction of twist is opposite to the direction of coiling. The heterochiral string can move oppositely to the homochiral string. The heterochiral string can be expanded as the string is heated and can be contracted as the string is cooled.

One of the strings, the first string (1101) and the second string (1103), forming the driving part (11) can be the homochiral string displaying that the directions of twist and coiling are same, and the other string can be the heterochiral string displaying that the directions of twist and coiling are different.

In an example of the present invention, the driving part (11) is composed of the first string (1101) and the second string (1103) having different structures, so that the driving part can realize the different drivings by same heat energy. The first string (1101) can be the homochiral string. At this time, the second string (1103) is the heterochiral string, so that the first string (1101) and the second string (1103) display different structures. It is also possible that the first string (1101) is the heterochiral string. At this time, the second string (1103) is the homochiral string, so that the first string (1101) and the second string (1103) display different structures.

The driving part (11) includes the thermoelectric element (not shown) generating heat with the current provided. The thermoelectric element (not shown) can deliver heat energy to the first string (1101) and the second string (1103).

In an example of the present invention, the driving part (11) can include the thermoelectric element (not shown) playing a role in converting electric energy into heat energy in the course of making the first string (1101) and the second string (1103) twisted and coiled. The thermoelectric element (not shown) can be included in the driving part (11) in the form of electrothermal wire or electrothermal coating. The thermoelectric element (not shown) can heat the first string (1101) and the second string (1103). The thermoelectric element (not shown) is connected to the first string (1101) and the second string (1103) separately, so that it can heat the first string (1101) and the second string (1103) separately.

FIG. 32 illustrates the unit body (1100) constructing the driving part (11) of the soft actuator (1) according to an example of the present invention.

FIG. 33 is a cross-sectional view of the soft actuator (1) according to an example of the present invention.

The driving part (11) can realize different behaviors, either contraction or expansion, between the first string (1101) and the second string (1103) forming the unit body (1100) when the first string (1101) and the second string (1103) are heated or cooled.

In an example of the present invention, the first string (1101) constituting the unit body (1100) of the driving part (11) can be contracted when it is heated. At this time, the driving part (11) can realize different behaviors when the first string (1101) and the second string (1103) are provided with the same heat energy since the second string (1103) forming the unit body (1100) is expanded by heating. Therefore, the first string (1101) and the second string (1103) constituting the unit body (1100) are not heated or cooled simultaneously, and instead they are heated or cooled independently to induce the driving of the soft actuator (1).

The driving part (11) can include several unit bodies (1100).

In an example of the present invention, the driving part (11) can include one or more unit bodies (1100). The driving part (11) is penetrated into the driving cable (12) and several unit bodies (1100) can be arranged apart. As the number of unit bodies (1100) included in the driving part (11) increases, the driving of the soft actuator (1) can be controlled more accurately. However, the number of unit bodies (1100) in the driving part (11) should not exceed the number of unit bodies that may be contained within the volume of the driving cable (12). Preferably, the driving part (11) includes at least three unit bodies (1100). The unit bodies (1100) are not arranged densely on one side of the driving cable (12) but uniformly disposed on the front surface of the driving cable (12) to realize driving of the soft actuator (1).

The driving part (11) makes the movement of the driving cable (12) such as tension, compression, bending, and rotation possible by the independent driving of several unit bodies (1100) therein.

The independent driving of those multiple unit bodies (1100) makes the tension, compression, bending, and rotation possible, which are illustrated in the following examples in more detail.

The driving cable (12) may have multiple hollows corresponding to the number of the unit bodies (1100).

In an example of the present invention, the driving cable (12) can have enough space to allow multiple unit bodies (1100) to be intruded. The driving cable (12) may have the same number of hollows as the number of unit bodies (1100) to be intruded. The hollows in the driving cable (12) can be uniformly formed on the entire surface of the driving cable (12) without being densely arranged on one side. The hollow of the driving cable (12) can penetrate one surface of the driving cable (12) and the other surface thereof. The driving cable (12) can wrap one surface or the other surface of the unit body, so that the unit body (1100) and the driving cable (12) are driven in the same track. A side wall can be made of a flexible material to prevent the resistance generated by the driving cable (12) in the soft actuator.

Hereinafter, the tension, compression, bending, and rotation of the soft actuator (1) are described in the following examples. The soft actuator (1) comprising the 4 unit bodies (1100) is described in each example in advance to describe the driving. As shown in the cross-sectional view, the unit body (1100) sitting at the direction of 12 o'clock is indicated as (a), and the unit bodies (1100) arranged regularly from the standard position (a) at the intervals of 90 degree clock-wise are indicate respectively as (b), (c), and (d).

<Example 3> Tension and Compression

FIG. 34 illustrates the compression or tension of the soft actuator (1) according to an example of the present invention.

In an example of the present invention, the first strings (1101) of the unit body (1100a)~the unit body (1100d) can be heated simultaneously. By that, the soft actuator (1) can be compressed or expanded. In particular, when all the first strings (1101) are composed of homochiral strings, the soft actuator (1) can be compressed by heating the first string (1101). At this time, the second strings (1103) have to be heterochiral strings, and the soft actuator (1) can be expanded by heating the second string (1103). On the other hand, when all the first strings (1101) are heterochiral strings, the soft actuator (1) can be expanded by heating the first string (1101). And at this time, the second strings (1103)

are necessarily homochiral strings and the soft actuator (1) can be compressed by heating the second string (1103).

The compression or expansion can be accomplished when a pair of the unit bodies (1100) facing each other are compressed or expanded. For example, the first strings (1101) or the second strings (1103) of the unit bodies (1100) (a) and (c) are heated simultaneously, the soft actuator (1) can be compressed or expanded. Also, when the first strings (1101) or the second strings (1103) of the unit bodies (1100) (b) and (d) are heated simultaneously, the soft actuator 91 can be compressed or expanded.

<Example 4> Bending

FIG. 35 illustrates the bending of the soft actuator (1) according to an example of the present invention.

In an example of the present invention, the bending movement of the soft actuator (1) can be achieved by contracting or expanding each unit body (1100). When all the first strings (1101) of the unit bodies (1100) are homochiral strings, the unit body (1100) (a) can be independently contracted by heating the first string (1101) of the unit body (1100) (a). At this time, all the second strings (1103) of those unit bodies (1100) are heterochiral strings. The not-heated unit bodies (1100) (b)~(d) are pulled to the direction of the contracted unit body (1100) (a) and then the soft actuator (1) is bending to the direction of (a). At this time, the unit body (1100) (c) can be further expanded by heating the second string (1103) of the unit body (1100) (c). By that, the degree of bending of the soft actuator (1) can be controlled.

By heating the second string (1103) of the unit body (1100) (c), the second string (1103) of the unit body (1100) (c) can be expanded independently. At this time, the non-heated unit bodies (1100) (a), (b), and (d) are pulled back to the opposite direction of the expanded unit body (1100) (c) and the soft actuator (1) realizes the bending movement to the direction of (a). By heating the first string (1101) of the unit body (1100) (a), the unit body (1100) (a) can be contracted. In this way, the degree of bending of the soft actuator (1) can be controlled.

By heating the second string (1103) of the unit body (1100) (a) to expand thereof and by expanding the second string (1103) of the unit body (1100) (c) with supplying a large amount of heat energy, the bending movement of the soft actuator (1) can be accomplished to the direction of (a) due to the difference in length of the expanded unit bodies (1100). The bending movement can be achieved with reference to the unit bodies (1100) (b), (c), and (d), and accordingly the bending movement is possible in 4 directions of up, down, left, and right.

When all the first strings (1101) are heterochiral strings and at the same time all the second strings (1103) are homochiral strings, the bending movement can be achieved in all four directions of up, down, left, and right by heating the first strings (1101) or the second strings (1103) of the unit bodies (1100) (a)~(d) according to the method described above.

In an example of the present invention, the bending movement of the soft actuator (1) can be achieved to other directions than the four directions above by heating the multiple neighboring unit bodies (1100) to contract or expand them. When all the first strings (1101) are homochiral strings and at the same time all the second strings (1103) are heterochiral strings, the unit bodies (a) and (b) can be contracted by heating the first strings (1101) of the unit bodies (1100) (a) and (b). At this time, the unit bodies (c) and (d) are pulled to the direction of (a) and (b), by which the soft actuator (1) realizes the right-upward bending movement. The direction of bending can be precisely controlled by regulating the amount of heat energy delivered to the unit bodies (1100) (a) and (b). Additionally, the right-upward bending movement of the soft actuator (1) can be increased by heating the second strings (1103) of the unit bodies (1100) (c) and (d) to cause them expanded.

In the meantime, the unit body (1100) (c) and the unit body (1100) (d) can be expanded by heating the second strings (1103) of the unit body (1100) (c) and the unit body (1100) (d). At this time, the unit bodies (1100) (a) and (b) are pulled back toward the direction of (a) and (b), by which the soft actuator (1) can achieve the right-upward bending movement. Also, the direction of bending movement can be controlled more accurately by regulating the amount of heat energy delivered to each of the unit body (1100) (c) and the unit body (1100) (d). Additionally, the right-upward bending movement of the soft actuator (1) can be increased by heating the first strings (1101) of the unit bodies (1100) (a) and (b) to cause them contracted.

By heating the second strings (1103) of the unit bodies (1100) (a) and (b) to expand thereof and by expanding the second strings (1103) of the unit bodies (1100) (c) and (d) with supplying a large amount of heat energy, the right-upward bending movement of the soft actuator (1) can be accomplished due to the difference in length of the expanded unit bodies (1100). The bending movement can be achieved with reference to all the unit bodies (1100), and accordingly the bending movement to all directions including up-right, down-right, up-left, and down-left directions can be accomplished.

When all the first strings (1101) are heterochiral strings and at the same time all the second strings (1103) are homochiral strings, the multi-directional bending movement can be achieved by heating the first string (1101) or the second strings (1103) of the unit bodies (a)~(d) according to the method described above.

<Example 5> Rotation

FIG. 36 illustrates the rotation of the soft actuator (1) according to an example of the present invention.

In an example of the present invention, the rotation movement of the soft actuator (1) can be achieved when the bending movement described above continues. First, the bending is achieved to the direction of the unit body (110) (a), and then the bending continues to the direction of the unit bodies (110) (b)~(d) serially, and then the soft actuator (1) rotates clockwise. To accomplish more accurate rotation, the two neighboring unit bodies (110) are heated simultaneously and the heat energy delivered to each unit body (110) is regulated, and then the bending direction can be slowly changed. On the other hand, when the bending continues to the direction of the unit bodies (110) (d)~(b) serially after the bending has been achieved to the direction of the unit body (110) (a), the soft actuator (1) rotates counter-clockwise. The bending direction can be gradually changed by adjusting the heat energy delivered to each unit body (110) while simultaneously heating the two adjacent unit bodies (110). In addition, the rotation speed of the soft actuator (1) can be controlled by changing the time interval for heating each unit body (110). And the rotation radius of the soft actuator (1) can be regulated by applying a method of controlling the degree of bending described above.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

BRIEF DESCRIPTION OF THE MARK OF DRAWINGS 1, 100, 200, 300, 400, 500, 600, 1000: soft actuator
110, 210, 310, 410, 510, 610, 710, 810, 910, 1010: string
111, 211, 311, 411, 511, 1101: first string
131. 231. 331. 431. 531, 1103: second string
120, 220, 320, 420, 520, 620, 1020: thermoelectric element
121, 621, 721a, 721b, 821, 921: first electrode
122, 622, 722a, 722b, 822, 922: P-type thermoelectric material
123, 623, 723a, 723b, 823, 923: N-type thermoelectric material
124, 624, 724a, 724b, 824, 924: second electrode
230, 830: control part
340, 940: adhesive layer
750: insulating layer
11: driving part
11a: first driving surface
11b: second driving surface
1100: unit body
131: first conductive body
133: conductor
135: second conductive body
15: power supply part
17: string part
12: driving cable
13: thermoelectric element part

What is claimed is:

1. A soft actuator comprising
a string that is contracted or expanded by heating or cooling, the string being twisted or twisted and coiled;
a thermoelectric element surrounding a surface of the string to heat or cool the string, the thermoelectric element contracting and expanding according to a contraction or an expansion of the string; and
a deformable adhesive layer to connect the thermoelectric element to the surface of the string.

2. The soft actuator according to claim 1, wherein the soft actuator additionally includes a control part to control the direction of current flowing in the thermoelectric element.

* * * * *